United States Patent
Hercouet et al.

(10) Patent No.: US 7,947,089 B2
(45) Date of Patent: May 24, 2011

(54) METHOD OF COLORING OR LIGHTENING IN THE PRESENCE OF AN INORGANIC BASE AND KIT

(75) Inventors: Leïla Hercouet, Neuilly Plaisance (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/642,592

(22) Filed: Dec. 18, 2009

(65) Prior Publication Data

US 2010/0154137 A1    Jun. 24, 2010

Related U.S. Application Data

(60) Provisional application No. 61/150,933, filed on Feb. 9, 2009, provisional application No. 61/150,939, filed on Feb. 9, 2009.

(30) Foreign Application Priority Data

Dec. 19, 2008   (FR) ..................................... 08 58886
Dec. 19, 2008   (FR) ..................................... 08 58892

(51) Int. Cl.
*A61Q 5/10* (2006.01)

(52) U.S. Cl. ............. 8/405; 8/406; 8/410; 8/411; 8/421; 8/426; 8/435; 8/455; 8/580; 8/604; 132/202; 132/208

(58) Field of Classification Search .............. 8/405, 406, 8/410, 411, 421, 426, 435, 455, 580, 604; 132/202, 208
See application file for complete search history.

(56) References Cited

U.S. PATENT DOCUMENTS

| | | | |
|---|---|---|---|
| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,845,293 A | 7/1989 | Junino et al. |
| 5,021,066 A | 6/1991 | Aeby et al. |
| 5,259,849 A * | 11/1993 | Grollier et al. ..................... 8/405 |
| 5,364,414 A | 11/1994 | Lang et al. |
| 5,817,155 A | 10/1998 | Yasuda et al. |
| 6,010,541 A | 1/2000 | De La Mettrie |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,766,977 B2 | 8/2010 | Cottard et al. |
| 7,799,095 B2 | 9/2010 | Mario et al. |
| 2003/0190297 A1 | 10/2003 | Narasimhan et al. |
| 2003/0226217 A1 | 12/2003 | Bowes et al. |

(Continued)

FOREIGN PATENT DOCUMENTS

CA    1 268 421    5/1990

(Continued)

OTHER PUBLICATIONS

French Search Report for FR 0858886, dated Nov. 3, 2009.
French Search Report for FR 0858892, dated Sep. 24, 2009.
English language abstract of DE 101 48 571 B4, Apr. 24, 2003.
English language abstract of DE 10 2006 012 575 A1, Feb. 8, 2007.
European Search Report for EP 09 17 9992, dated Mar. 24, 2010.
English language abstract of DE 101 48 671 A1, Apr. 10, 2003.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.

(Continued)

*Primary Examiner* — Eisa B Elhilo
(74) *Attorney, Agent, or Firm* — Finnegan, Henderson, Farabow, Garrett & Dunner

(57) ABSTRACT

The present disclosure relates to a method of coloring or lightening of human keratin fibers in the presence of an oxidizing agent, comprising the application of an anhydrous cosmetic composition comprising at least one fat, and at least one surfactant, an oxidizing composition, a composition comprising at least one inorganic base. It also relates to a kit with several compartments, in which a first compartment comprises the aforementioned anhydrous cosmetic composition, a second compartment comprises an oxidizing composition and a third compartment comprises a composition comprising at least one inorganic base and optionally at least one dye.

24 Claims, No Drawings

U.S. PATENT DOCUMENTS

| | | |
|---|---|---|
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2004/0234700 A1 | 11/2004 | Tchapian et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 A | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 B4 | 4/2003 |
| DE | 101 48 671 A1 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 A1 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 B1 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 A1 | 6/2004 |
| EP | 1 438 951 A1 | 7/2004 |
| EP | 1 449 512 | 8/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 B1 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 A1 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |

| WO | WO 2008/021641 | 2/2008 |
| WO | WO 2008/096497 | 8/2008 |
| WO | WO 2008/138844 | 11/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 023 891, dated Aug. 2, 2000.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 18 0003, dated Feb. 24, 2010.
European Search Report for EP 10 15 5935, dated Octoer 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 8, 2010, in U.S. Appl. No. 12/642,473.
Notice of Allowance mailed in co-pending U.S. Appl. No. 12/339,753, dated Jul. 9, 2010.

Notice of Allowance mailed Jun. 11, 2010, in U.S. Appl. No. 12/642,489.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Nov. 22, 2010, in co-pending U.S. Appl. No. 12/642,593.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

METHOD OF COLORING OR LIGHTENING IN THE PRESENCE OF AN INORGANIC BASE AND KIT This application claims benefit of U.S. Provisional Application Nos. 61/150,933, filed Feb. 9, 2009, and 61/150,939, filed Feb. 9, 2009. This application also claims benefit of priority under 35 U.S.C. §119 to French Patent Application Nos. 0858892, filed Dec. 19, 2008 and 0858886, filed Dec. 19, 2008.

The present disclosure relates to a method of coloring or lightening of human keratin fibers in the presence of an oxidizing agent, comprising the application of:
an anhydrous cosmetic composition (A) comprising at least one fat and at least one surfactant,
a composition (B) comprising at least one oxidizing agent, and
a composition (C) comprising at least one inorganic base and optionally at least one dye.

The present disclosure also relates to a kit with several compartments, in which a first compartment comprises an anhydrous cosmetic composition (A) comprising at least one fat and at least one surfactant, a second compartment comprises a composition (B) comprising at least one oxidizing agent, and a third compartment comprises a composition (C) comprising at least one inorganic base and optionally at least one dye.

Among the methods of coloring human keratin fibers, such as the hair, mention may be made of permanent or oxidation dyeing. For example, this method of coloring employs at least one oxidation dye precursor, generally at least one oxidation base optionally combined with at least one coupler.

In general, oxidation bases are chosen from ortho- or para-phenylenediamines, ortho- or para-aminophenols as well as heterocyclic compounds. These oxidation bases are colorless or faintly colored compounds which, when combined with oxidants, give colored species, by a process of oxidative condensation.

Quite often, the shades obtained with these oxidation bases may be varied by combining them with at least one coupler, the latter possibly being selected from aromatic meta-diamines, meta-aminophenols, meta-diphenols and heterocyclic compounds, such as indole compounds.

The variety of molecules employed for the oxidation bases and couplers makes it possible to obtain a rich palette of colors.

Direct or semi-permanent dyeing is also known. The method used conventionally in direct dyeing consists of applying, on the keratin fibers, direct dyes, which are colored and coloring molecules that have an affinity for the fibers, pausing to allow the molecules to penetrate, by diffusion, to the interior of the fiber, and then rinsing.

The direct dyes generally used are chosen from the nitrobenzene, anthraquinone, nitropyridine, azo, methine, azomethine, xanthene, acridine, azine or triarylmethane direct dyes.

This type of method may not require the use of an oxidizing agent for developing the coloration. However, its use in order to obtain a lightening effect with the dyeing is not necessarily excluded. This is then called direct or semi-permanent dyeing in lightening conditions.

The methods of permanent or also semi-permanent dyeing in lightening conditions therefore may consist of using, with the dyeing composition, an aqueous composition comprising at least one oxidizing agent, in conditions of alkaline pH in the vast majority of cases. This oxidizing agent may have the role of breaking down the melanin of the hair, which, depending on the nature of the oxidizing agent present, leads to more or less pronounced lightening of the fibers. Thus, for relatively slight lightening, the oxidizing agent is generally hydrogen peroxide. When more pronounced lightening is required, generally peroxidized salts are employed, such as persulphates for example, in the presence of hydrogen peroxide.

The methods of lightening human keratin fibers may consist of using an aqueous composition comprising at least one oxidizing agent, in conditions of alkaline pH in the vast majority of cases. This oxidizing agent has the role of breaking down the melanin of the hair, which, depending on the nature of the oxidizing agent present, leads to more or less pronounced lightening of the fibes. Thus, for relatively slight lightening, the oxidizing agent is generally hydrogen peroxide. When more pronounced lightening is required, generally peroxidized salts are used, such as persulphates for example, in the presence of hydrogen peroxide.

One difficulty arises from the fact that these methods of coloring or lightening are employed in alkaline conditions and the alkaline agent most commonly used is ammonia. Thus, it may allow the pH of the composition to be adjusted to alkaline pH so as to permit activation of the oxidizing agent. However, this agent also may cause swelling of the keratin fiber, with lifting of the scales, which may promote the penetration of the oxidant, as well as—when present—dyes, such as oxidation dyes, to the interior of the fiber, and may increase the efficacy of the lightening or coloring reaction.

Now, this alkalizing agent may be very volatile, which may be a disadvantage for the user because of the characteristic strong, rather unpleasant odor of the ammonia that is released during the process.

Moreover, the amount of ammonia released may necessitate the use of higher contents than necessary to make up for this loss. This is not without consequence for the user, who not only is inconvenienced by the odor but may also be exposed to greater risks of intolerance, for example irritation of the scalp such as tingling.

As for the option of purely and simply replacing the ammonia wholly or partly with at least one other conventional alkalizing agent, this does not provide compositions that are as effective as those based on ammonia, for example, because these alkalizing agents do not give sufficient lightening of the pigmented fibers in the presence of the oxidizing agent.

One objective of the present disclosure is to propose methods of lightening or coloring in the presence of an oxidizing agent that do not have drawbacks of the existing methods having the presence of high contents of ammonia. Under this objective, the disclosed methods remaining at least as effective with respect to lightening and the uniformity of the existing methods having the presence of high contents of ammonia, or in the case of coloring, the disclosed methods remaining at least as effective with respect to the strength of the coloration obtained, the chromaticity, as well as the uniformity of coloration along the fiber. Following this objective, the methods according to the disclosure lead to strong coloration.

These aims and others can be achieved by the present disclosure, which relates to a method of coloring or lightening of human keratin fibers in the presence of an oxidizing agent, in which the following are applied on said fibers:
an anhydrous cosmetic composition (A) comprising at least one fat, and at least one surfactant;
a composition (B) comprising at least one oxidizing agent;
a composition (C) comprising at least one inorganic base.

The present disclosure also relates to a kit comprising several compartments comprising in a first compartment an anhydrous composition (A) comprising at least one fat, and at least one surfactant, in a second compartment a composition (B) comprising at least one oxidizing agent, and in a third compartment a composition (C) comprising at least one inorganic base and optionally at least one oxidation dye and/or at least one direct dye.

Other characteristics of the present disclosure will become clearer on reading the description and the examples given hereunder.

Hereinafter, and unless stated otherwise, the limits of a range of values are included in this range.

The human keratin fibers treated by the method according to the disclosure may be hair fibers.

As stated previously, the method of coloring or lightening may be applied in the presence of an anhydrous composition (A).

For example, an "anhydrous composition" may mean, in the sense of the disclosure, a composition having a water content of below 5 wt. %, such as below 2 wt. %, below 1 wt. %, and zero wt %, relative to the weight of said composition. It should be noted that the water can also be in the form of bound water, such as the water of crystallization of salts or traces of water absorbed by the raw materials used in the preparation of the compositions according to the disclosure.

Moreover, in certain embodiments when the disclosed composition is used for lightening, the disclosed composition does not comprise a direct dye or oxidation dye precursor (bases and couplers) usually employed for the coloring of human keratin fibers. In alternative embodiments, if the disclosed composition does comprise a direct dye or oxidation dye precursor, their total content does not exceed 0.005 wt. % relative to the weight of the anhydrous composition and of the aqueous composition comprising the oxidizing agent. At such a content, it is likely that only the composition would possibly be colored, i.e., an effect of coloring of keratin fibers would likely not be observed.

The method of lightening may be employed without an oxidation base, coupler, or direct dye.

As has been mentioned, the anhydrous cosmetic composition (A) comprises at least one fat.

"Fats" are organic compounds insoluble in water at normal temperature (25° C.) and at atmospheric pressure (760 mmHg) (solubility below 5% such as below 1% or below 0.1%). In their structure they have at least one chain of at least two siloxane groups or at least one hydrocarbon chain having at least 6 carbon atoms. Moreover, fats are generally soluble in organic solvents in the same conditions of temperature and pressure, for example chloroform, ethanol, benzene, liquid paraffin or decamethyl cyclopentasiloxane.

The fats may be chosen from the lower $C_6$-$C_{16}$ alkanes, non-silicone oils of animal, vegetable, mineral or synthetic origin, fatty alcohols, fatty acids, fatty acid and/or fatty alcohol esters, non-silicone waxes, silicones, or mixtures thereof.

According to this disclosure, the alcohols, esters and fatty acids may have at least one linear or branched, saturated or unsaturated hydrocarbon group, comprising 6 to 30 carbon atoms, optionally substituted, for example, with at least one hydroxyl group (such as 1 to 4). If they are unsaturated, these compounds can comprise one to three conjugated or unconjugated carbon-carbon double bonds.

Regarding the $C_6$-$C_{16}$ lower alkanes, these are linear, branched, optionally cyclic. As examples, mention may be made of hexane, undecane, dodecane, tridecane, isoparaffins such as isohexadecane, isodecane.

As non-silicone oils of animal, vegetable, mineral or synthetic origin, usable in the composition of the disclosure, illustrative examples include:

hydrocarbon oils of animal origin, such as perhydrosqualene;

triglyceride oils of vegetable or synthetic origin, such as the liquid triglycerides of fatty acids having from 6 to 30 carbon atoms such as the triglycerides of heptanoic or octanoic acids or alternatively, for example, sunflower oil, maize oil, soya oil, cucurbit oil, grapeseed oil, sesame oil, hazelnut oil, apricot oil, macadamia oil, arara oil, sunflower oil, castor oil, avocado oil, the triglycerides of caprylic/capric acids such as those sold by the company Stearineries Dubois or those sold under the names MIGLYOL® 810, 812 and 818 by the company Dynamit Nobel, jojoba oil, shea butter oil;

linear or branched hydrocarbons, of mineral or synthetic origin, with more than 16 carbon atoms, such as the volatile or non-volatile paraffin oils, and their derivatives, petroleum jelly, liquid paraffin, polydecenes, hydrogenated polyisobutene such as PARLEAM®; such as paraffin oils, petroleum jelly, liquid paraffin, polydecenes, hydrogenated polyisobutenes such as PARLEAM; and fluorinated oils such as perfluoromethylcyclopentane and perfluoro-1,3-dimethylcyclohexane, sold under the names "FLUTEC® PC1" and "FLUTEC® PC3" by the Company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoromethoxybutane and nonafluoroethoxyisobutane; derivatives of perfluoromorpholine, such as 4-trifluoromethyl perfluoromorpholine sold under the name "PF 5052®" by the 3M Company.

The fatty alcohols suitable for the present disclosure may be chosen from the saturated or unsaturated, linear or branched alcohols having from 8 to 30 carbon atoms. Non-limiting examples include cetyl alcohol, stearyl alcohol and their mixture (cetylstearyl alcohol), octyldodecanol, 2-butyloctanol, 2-hexyldecanol, 2-undecylpentadecanol, oleyl alcohol, or linoleyl alcohol.

With regard to the fatty acid and/or fatty alcohol esters, such as those different from the triglycerides mentioned above; mention may be made of the esters of aliphatic saturated or unsaturated, linear or branched $C_1$-$C_{26}$ mono- or polyacids and of aliphatic saturated or unsaturated, linear or branched $C_1$-$C_{26}$ mono- or polyalcohols, the total number of carbons in the esters being greater than or equal to 10.

Among the monoesters, non-limiting examples include dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, myristyl, stearyl myristate, hexyl stearate, butyl stearate, isobutyl stearate; dioctyl malate, hexyl laurate, 2-hexyldecyl laurate.

Still within the scope of this variant, examples also include the esters of $C_4$-$C_{22}$ di- or tricarboxylic acids and of $C_1$-$C_{22}$ alcohols and the esters of mono-, di- or tricarboxylic acids and $C_2$-$C_{26}$ di-, tri-, tetra-, or pentahydroxy alcohols.

Non-limiting examples include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, the following ester may be used in certain embodiments: ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of $C_6$-$C_{30}$, such as $C_{12}$-$C_{22}$ fatty acids. It should be noted that "sugar" means oxidized hydrocarbon compounds that possess several alcohol functions, with or without an aldehyde or ketone function, and which have at least 4 carbon atoms. These sugars can be monosaccharides, oligosaccharides, or polysaccharides.

As suitable sugars, mention may be made, for example, of sucrose, glucose, galactose, ribose, fucose, maltose, fructose, mannose, arabinose, xylose, lactose, and their derivatives, such as alkylated, for example methylated derivatives such as methylglucose.

The esters of sugars and of fatty acids may be chosen from the group comprising the esters or mixtures of esters of sugars described previously and of linear or branched, saturated or unsaturated $C_6$-$C_{30}$, such as $C_{12}$-$C_{22}$, fatty acids. If they are unsaturated, these compounds can comprise one to three conjugated or unconjugated carbon-carbon double bonds.

The esters according to this variant can also be chosen from the mono-, di-, tri-, and tetra-esters, the polyesters and mixtures thereof.

These esters can be chosen from, for example, oleate, laurate, palmitate, myristate, behenate, cocoate, stearate, linoleate, linolenate, caprate, arachidonate, or mixtures thereof such as the oleo-palmitate, oleo-stearate, palmito-stearate mixed esters.

For example, the mono- and di-esters may be used, such as mono- or di-oleate, stearate, behenate, oleopalmitate, linoleate, linolenate, oleostearate, of sucrose, of glucose or of methylglucose.

Non-limiting examples include the product sold under the name GLUCATE® DO by the company Amerchol, which is a methylglucose dioleate.

Non-limiting examples of esters or of mixtures of esters of sugar of fatty acid include:
  the products sold under the names F160, F140, F110, F90, F70, SL40 by the company Crodesta, denoting respectively the palmito-stearates of sucrose formed of 73% of monoester and 27% of di- and tri-ester, of 61% of monoester and 39% of di-, tri-, and tetra-ester, of 52% of monoester and 48% of di-, tri-, and tetra-ester, of 45% of monoester and 55% of di-, tri-, and tetra-ester, of 39% of monoester and 61% of di-, tri-, and tetra-ester, and the mono-laurate of sucrose;
  the products sold under the name RYOTO SUGAR ESTERS for example with the reference B370 and corresponding to the behenate of sucrose formed from 20% of monoester and 80% of di-triester-polyester; and
  the sucrose mono-di-palmito-stearate marketed by the company Goldschmidt under the name TEGOSOFT® PSE.

The non-silicone wax or waxes may be chosen from carnauba wax, candelilla wax, and alfa wax, paraffin wax, ozokerite, vegetable waxes such as olive wax, rice wax, hydrogenated jojoba wax or absolute waxes of flowers such as essential wax of blackcurrant flower sold by the company BERTIN (France), animal waxes such as beeswaxes, or modified beeswaxes (cerabellina); other waxes or waxy raw materials that can be used according to the disclosure are for example marine waxes such as that sold by the company SOPHIM under reference M82, the waxes of polyethylene or of polyolefins in general.

The silicones for use in the cosmetic compositions of the present disclosure are volatile or non-volatile, cyclic, linear or branched silicones, modified with organic groups or unmodified, having a viscosity from $5.10^{-6}$ to $2.5\ m^2/s$ at 25° C., such as $1.10^{-5}$ to $1\ m^2/s$.

The silicones that can be used according to the disclosure can be in the form of oils, waxes, resins, or gums.

For example, the silicone can be chosen from the polydialkylsiloxanes, such as the polydimethylsiloxanes (PDMS), and the organo-modified polysiloxanes having at least one functional group can be chosen from the poly(alkoxylated) groups, the amines groups and the alkoxy groups.

The organopolysiloxanes are defined in more detail in the work of Walter NOLL "Chemistry and Technology of Silicones" (1968), Academic Press. They can be volatile or non-volatile.

When they are volatile, the silicones may be chosen from those having a boiling point ranging from 60° C. to 260° C., such as, for example, (i) the cyclic polydialkylsiloxanes having from 3 to 7, such as from 4 to 5 silicon atoms. These are, for example, octamethylcyclotetrasiloxane such as those marketed under the name VOLATILE SILICONE® 7207 by UNION CARBIDE or SILBIONE® 70045 V2 by RHODIA, decamethylcyclopentasiloxane marketed under the name VOLATILE SILICONE® 7158 by UNION CARBIDE, and SILBIONE® 70045 V5 by RHODIA, and mixtures thereof.

Mention is also made to the cyclocopolymers of the dimethylsiloxanes/methylalkylsiloxane type, such as SILICONE VOLATILE® FZ 3109 marketed by the company UNION CARBIDE, of formula:

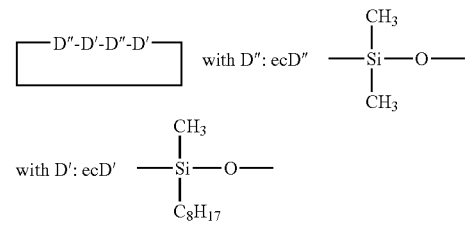

Additional mention may be made to the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2', 3,3'-trimethylsilyloxy) bis-neopentane.

The silicones may also be chosen from (ii) the volatile linear polydialkylsiloxanes with 2 to 9 silicon atoms and with a viscosity less than or equal to $5.10^{-6}\ m^2/s$ at 25° C. These include, for example, decamethyltetrasiloxane marketed for example under the name "SH 200" by the company TORAY SILICONE. Silicones included in this class are also described in the article published in Cosmetics and Toiletries, Vol. 91, Jan. 76, p. 27-32—TODD & BYERS "Volatile Silicone fluids for cosmetics".

Non-volatile polydialkylsiloxanes, gums and resins of polydialkylsiloxanes, polyorganosiloxanes modified with the aforementioned organofunctional groups and mixtures thereof may be used.

These silicones may be chosen from the polydialkylsiloxanes, such as polydimethylsiloxanes with trimethylsilyl end groups. The viscosity of the silicones is measured at 25° C. according to standard ASTM 445 Appendix C.

Among these polydialkylsiloxanes, non-limiting examples include the following commercial products:
- the SILBIONE® oils of the series 47 and 70 047 or the MIRASIL® oils marketed by RHODIA such as for example the oil 70 047 V 500 000;
- the oils of the MIRASIL® series marketed by the company RHODIA;
- the oils of the 200 series from the company DOW CORNING such as DC200 with a viscosity of 60 000 mm²/s; and
- the VISCASIL® oils from GENERAL ELECTRIC and certain oils of the SF series (SF 96, SF 18) from GENERAL ELECTRIC.

Mention may also be made to the polydimethylsiloxanes with dimethylsilanol end groups known by the name dimethiconol (CTFA), such as the oils of the 48 series from the company RHODIA.

In this class of polydialkylsiloxanes, non-limiting examples include the products marketed under the names "ABIL WAX® 9800 and 9801" by the company GOLDSCHMIDT, which are polydialkyl ($C_1$-$C_{20}$) siloxanes.

The silicone gums that can be used according to the disclosure include, for example, polydialkylsiloxanes, such as polydimethylsiloxanes having high number-average molecular weights ranging from 200,000 and 1,000,000 used alone or mixed in a solvent. The solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or mixtures thereof.

Products which may be usable according to the disclosure include mixtures such as:
- mixtures formed from a chain end hydroxylated polydimethylsiloxane, or dimethiconol (CTFA) and a cyclic polydimethylsiloxane, also called cyclomethicone (CTFA), such as the product Q2 1401 marketed by the company DOW CORNING;
- mixtures of a polydimethylsiloxane gum and a cyclic silicone such as the product SF 1214 Silicone Fluid from the company GENERAL ELECTRIC, this product is a gum SF 30 corresponding to a dimethicone, having a number-average molecular weight of 500,000, dissolved in oil SF 1202 Silicone Fluid corresponding to decamethylcyclopentasiloxane;
- mixtures of two PDMS of different viscosities, such as a PDMS gum and a PDMS oil, such as the product SF 1236 from the company GENERAL ELECTRIC. The product SF 1236 is a mixture of a gum SE 30 as defined above having a viscosity of 20 m²/s and an oil SF 96 with a viscosity of $5.10^{-6}$ m²/s. Said product may comprise 15% of gum SE 30 and 85% of oil SF 96.

The organopolysiloxane resins that can be used according to the disclosure are crosslinked siloxane systems comprising the units:

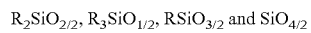

$R_2SiO_{2/2}$, $R_3SiO_{1/2}$, $RSiO_{3/2}$ and $SiO_{4/2}$ in which R represents an alkyl with 1 to 16 carbon atoms. Among these products, R may denote a $C_1$-$C_4$ lower alkyl group, such as methyl.

Among these resins, non-limiting examples include the product marketed under the name "DOW CORNING 593" or those marketed under the names "SILICONE FLUID SS 4230 and SS 4267" by the company GENERAL ELECTRIC, which are silicones with a dimethyl/trimethyl siloxane structure.

Non-limiting examples also include the resins of the trimethylsiloxysilicate type, such as those marketed under the names X22-4914, X21-5034 and X21-5037 by the company SHIN-ETSU.

The organomodified silicones that can be used according to the disclosure can be silicones as defined previously, whose structure includes at least one organofunctional groups fixed by means of a hydrocarbon group.

Apart from the silicones described above, the organomodified silicones can be polydiaryl siloxanes, such as polydiphenylsiloxanes, and polyalkylarylsiloxanes functionalized with the organofunctional groups mentioned previously.

The polyalkylarylsiloxanes are chosen for example from polydimethyl/methylphenylsiloxanes, polydimethyl/diphenylsiloxanes, linear and/or branched with viscosity in the range from $1.10{-}5$ to $5.10{-}2$ m²/s at 25° C.

Among these polyalkylarylsiloxanes non-limiting examples include the products marketed under the following names:
- the SILBIONE® oils of series 70 641 from RHODIA;
- the oils of the series RHODORSIL® 70 633 and 763 from RHODIA;
- the oil DOW CORNING 556 COSMETIC GRADE FLUID from DOW CORNING;
- the silicones of the PK series from BAYER such as the product PK20;
- the silicones of the PN, PH series from BAYER such as the products PN1000 and PH1000; and
- certain oils of the SF series from GENERAL ELECTRIC such as SF 1023, SF 1154, SF 1250, SF 1265.

Among the organomodified silicones, non-limiting examples include the polyorganosiloxanes having:
- polyethyleneoxy and/or polypropyleneoxy groups optionally having $C_6$-$C_{24}$ alkyl groups, such as the products called dimethicone copolyol marketed by the company DOW CORNING under the name DC 1248 or the oils SILWET® L 722, L 7500, L 77, L 711 from the company UNION CARBIDE and the alkyl($C_{12}$)-methicone copolyol marketed by the company DOW CORNING under the name Q2 5200;
- substituted or unsubstituted amine groups such as the products marketed under the name GP 4 Silicone Fluid and GP 7100 by the company GENESEE or the products marketed under the names Q2 8220 and DOW CORNING 929 or 939 by the company DOW CORNING. The substituted amine groups may be $C_1$-$C_4$ aminoalkyl groups;
- alkoxylated groups, such as the product marketed under the name "SILICONE COPOLYMER F-755" by SWS SILICONES and ABIL WAX® 2428, 2434 and 2440 by the company GOLDSCHMIDT.

In certain embodiments, the fats may possibly not comprise a $C_2$-$C_3$ alkoxylated unit and do not comprise a glycerol unit.

The fats may be chosen from compounds that are liquid or pasty at room temperature and atmospheric pressure.

The fat may be a compound that is liquid at a temperature of 25° C. and at atmospheric pressure.

The fat may be chosen from the $C_6$-$C_{16}$ lower alkanes, the non-silicone oils of mineral origin with more than 16 carbon atoms, or of vegetable, or synthetic origin, fatty alcohols, fatty acid and/or fatty alcohol esters, silicones, or mixtures thereof.

The fat may be chosen from liquid paraffin, polydecenes, fatty acid and/or fatty alcohol liquid esters, or mixtures thereof.

The fat of the composition according to the disclosure may be non-silicone.

The anhydrous cosmetic composition has a fats content which may range from 10 to 99 wt. % by weight relative to the weight of the anhydrous composition (A), for example a fats content ranging from 20 to 90 wt. %, or ranging from 25 to 80 wt. %.

The anhydrous cosmetic composition (A) can also comprise at least one surfactant.

The surfactant may be chosen from nonionic surfactants or from the anionic surfactants.

The anionic surfactant may be chosen from the salts (for example salts of alkali metals, such as of sodium, salts of ammonium, salts of amines, salts of aminoalcohols or salts of alkaline-earth metals such as magnesium) of the following compounds:

alkylsulphates, alkylethersulphates, alkylamidoethersulphates, alkylaryl-polyethersulphates, monoglyceride sulphates;

alkylsulphonates, alkylamidesulphonates, alkylarylsulphonates, α-olefin-sulphonates, paraffin-sulphonates;

alkylphosphates, alkyletherphosphates;

alkylsulphosuccinates, alkylethersulphosuccinates, alkylamide-sulphosuccinates;

alkylsulphosuccinamates;

alkylsulphoacetates;

acylsarcosinates; acylisethionates and N-acyltaurates;

salts of fatty acids such as oleic, ricinoleic, palmitic, stearic acids, copra oil acid or hydrogenated copra oil acid;

salts of alkyl D galactoside uronic acids;

acyl-lactylates;

salts of polyalkoxylated alkyl ether carboxylic acids, polyalkoxylated alkaryl ether carboxylic acids, polyalkoxylated alkylamidoether carboxylic acids, such as those having from 2 to 50 ethylene oxide groups;

and mixtures thereof.

It should be noted that the alkyl or acyl radical of these various compounds may have from 6 to 24 carbon atoms, such as from 8 to 24 carbon atoms, and the aryl radical may possibly denotes a phenyl or benzyl group.

The nonionic surfactants are for example chosen from the mono- or polyalkoxylated, mono- or polyglycerol nonionic surfactants. The alkoxylated units may be ethoxylated, propoxylated units, or a combination thereof, such as ethoxylated.

Non-limiting examples of alkoxylated nonionic surfactants include:

alkoxylated alkyl($C_8$-$C_{24}$)phenols, saturated or unsaturated, linear or branched, alkoxylated $C_8$-$C_{30}$ alcohols, saturated or unsaturated, linear or branched, alkoxylated $C_8$-$C_{30}$ amides, esters of saturated or unsaturated, linear or branched $C_8$-$C_{30}$ acids and of polyethylene glycols, esters of saturated or unsaturated, linear or branched $C_8$-$C_{30}$ acids and of polyethoxylated sorbitol, saturated or unsaturated, ethoxylated vegetable oils, condensates of ethylene oxide and/or of propylene oxide, among others, alone or mixed.

The surfactants may have a number of moles of ethylene oxide and/or propylene oxide between 1 and 100, such as between 2 and 50. For example, the nonionic surfactants do not comprise propoxylated units.

According to one embodiment of the disclosure, the alkoxylated nonionic surfactants may be chosen from the ethoxylated $C_8$-$C_3$ alcohols, the esters of saturated or unsaturated, linear or branched $C_8$-$C_{30}$ acids, and of polyethoxylated sorbitol.

As examples of nonionic mono- or polyglycerol surfactants, the $C_8$-$C_{40}$ mono- or polyglycerol alcohols may be used.

For example, the $C_8$-$C_{40}$ mono- or polyglycerol alcohols correspond to the following formula:

in which R represents a linear or branched, $C_8$-$C_{40}$ alkyl or alkenyl radical, such as $C_8$-$C_{30}$ alkyl or alkenyl radical, and m represents a number ranging from 1 to 30, such as from 1 to 10.

Non-limiting examples of compounds that are suitable within the scope of the disclosure include lauryl alcohol with 4 moles of glycerol (INCI name: POLYGLYCERYL-4 LAURYL ETHER), lauryl alcohol with 1.5 moles of glycerol, oleyl alcohol with 4 moles of glycerol (INCI name: POLYGLYCERYL-4 OLEYL ETHER), oleyl alcohol with 2 moles of glycerol (INCI name: POLYGLYCERYL-2 OLEYL ETHER), cetearyl alcohol with 2 moles of glycerol, cetearyl alcohol with 6 moles of glycerol, oleocetyl alcohol with 6 moles of glycerol, and octadecanol with 6 moles of glycerol.

The alcohol can represent a mixture of alcohols and the value of m represents a statistical value, which means that in a commercial product, several species of polyglycerol fatty alcohols can coexist as a mixture.

In certain embodiments, among the mono- or polyglycerol alcohols, it is possible to use the $C_8$/$C_{10}$ alcohol with one mole of glycerol, the $C_{10}$/$C_{12}$ alcohol with 1 mole of glycerol and the $C_{12}$ alcohol with 1.5 moles of glycerol.

For example, the surfactant comprised in the anhydrous composition may be a nonionic surfactant.

The content of surfactants in the anhydrous composition (A) may range from 0.1 to 50 wt. % relative to the weight of the anhydrous composition, such as an amount ranging from 0.5 to 30 wt. %.

The cosmetic composition (A) can also comprise various additives used conventionally in compositions for coloring or lightening the hair, such as anionic, cationic, nonionic, amphoteric, zwitterionic polymers or mixtures thereof; mineral thickening agents, and fillers such as clays, talc; organic thickening agents, such as with anionic, cationic, nonionic and amphoteric associative polymeric thickeners; antioxidants; penetrating agents; sequestering agents; perfumes; dispersants; film-forming agents; conditioning agents; ceramides; preservatives; and opacifiers.

Each of the above additives, if present in the composition, are individually present in an amount ranging from 0.01 to 20 wt. % relative to the weight of composition (A).

The composition can comprise at least one mineral thickening agent chosen from organophilic clays, pyrogenic silicas, or mixtures thereof.

The organophilic clay can be chosen from montmorillonite, bentonite, hectorite, attapulgite, sepiolite, and mixtures thereof. The clay may be a bentonite or a hectorite.

These clays can be modified with a chemical compound chosen from the quaternary amines, tertiary amines, aminoacetates, imidazolines, amine soaps, fatty sulphates, alkaryl sulphonates, amine oxides, and mixtures thereof.

As organophilic clays, non-limiting examples include the quaternium-18 bentonites such as those sold under the names BENTONE 3, BENTONE 38, BENTONE 38V by the company Rheox, TIXOGEL VP by the company United Catalyst, CLAYTONE 34, CLAYTONE 40, CLAYTONE XL by the company Southern Clay; the stearalkonium bentonites such as those sold under the names BENTONE 27 by the company Rheox, TIXOGEL LG by the company United Catalyst, CLAYTONE AF, CLAYTONE APA by the company Southern Clay; the quaternium-18/benzalkonium bentonites such as those sold under the names CLAYTONE HT, CLAYTONE PS by the company Southern Clay, the Quaternium-18 Hectorites such as those sold under the names BENTONE GEL DOA, BENTONE GEL ECO5, BENTONE GEL EUG, BENTONE GEL IPP, BENTONE GEL ISD, BENTONE GEL SS71, BENTONE GEL VS8, BENTONE GEL VS38 by the company Rheox and SIMAGEL M, SIMAGEL SI 345 by the company Biophil.

The pyrogenic silicas can be obtained by high-temperature hydrolysis of a volatile silicon compound in an oxyhydrogen flame, producing a finely divided silica. This method makes it possible to obtain hydrophilic silicas that have a large number of silanol groups on their surface. These hydrophilic silicas are for example marketed under the names "AEROSIL 130®", "AEROSIL 200®", "AEROSIL 255®", "AEROSIL 300®", "AEROSIL 380®" by the company Degussa, "CAB-O-SIL HS-5®", "CAB-O-SIL EH-5®", "CAB-O-SIL LM-130®", "CAB-O-SIL MS-55®", "CAB-O-SIL M-5®" by the company Cabot.

The surface of the silica can be modified chemically by chemical reaction in order to reduce the number of silanol groups. For example silanol groups can be replaced with hydrophobic groups: a hydrophobic silica is then obtained.

The hydrophobic groups can be chosen from:
trimethylsiloxyl groups, which may be obtained by pyrogenic treatment in the presence of hexamethyldisilazane. Silicas thus treated are called "Silica silylate" according to the CTFA (6th edition, 1995). They are for example marketed under the references "AEROSIL R812®" by the company Degussa, "CAB-O-SIL TS-530®" by the company Cabot.
dimethylsilyloxyl or polydimethylsiloxane groups, which may be obtained by treatment of pyrogenic silica in the presence of polydimethylsiloxane or dimethyldichlorosilane. Silicas thus treated are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SIL TS-720®" by the company Cabot.

The pyrogenic silica may have a particle size that can range from nanometric to micrometric, for example from approximately 5 to 200 nm.

The composition may include a hectorite, an organomodified bentonite or a pyrogenic silica, optionally modified.

When present, the mineral thickening agent can range from 1 to 30 wt. % relative to the weight of the composition.

The composition may be in the form of a gel or a cream.

As stated previously, the method according to the disclosure is carried out in the presence of a composition (B) comprising at least one oxidizing agent.

The oxidizing agent or agents may be chosen from hydrogen peroxide, urea peroxide, bromates or ferricyanides of alkali metals, peroxidized salts such as for example the persulphates, the perborates and the percarbonates of alkali metals or alkaline-earth metals, as well as the peracids and their precursors. At least one oxidation-reduction enzyme such as the laccases, peroxidases and oxidoreductases with 2 electrons (such as uricase), optionally in the presence of their respective donor or cofactor, can also be used as oxidizing agents.

This oxidizing agent may constitute hydrogen peroxide and if in aqueous solution (hydrogen peroxide), the concentration of which can vary, ranging from 0.1 to 50 wt. % relative to the oxidizing composition (B), such as ranging from 0.5 to 20 wt. %, and ranging from 1 to 15 wt. %.

Depending on the desired degree of lightening, the oxidizing agent can also comprise an oxidizing agent, for example chosen from the peroxidized salts.

For example, the oxidizing agent is chosen from the peroxidized salts and the peracids and precursors.

The oxidizing composition can be aqueous or non-aqueous. "Aqueous composition" means a composition having more than 5 wt. % of water, such as more than 10 wt. % of water, or more than 20 wt. % of water.

Composition (B) may be an aqueous composition.

It can also comprise at least one organic solvent.

As organic solvents, non-limiting examples include the linear or branched $C_2$-$C_4$ alkanols, such as ethanol and isopropanol; glycerol; polyols and ethers of polyols such as 2-butoxyethanol, propylene glycol, dipropylene glycol, monomethyl ether of propylene glycol, monoethyl ether and monomethyl ether of diethylene glycol, as well as aromatic alcohols such as benzyl alcohol or phenoxyethanol, and mixtures thereof.

The solvent or solvents, if present, usually have a content in the range from 1 to 40 wt. % relative to the weight of the oxidizing composition (C), such as ranging from 5 to 30 wt. %.

The oxidizing composition (B) can comprise at least one acidifying agents.

Among the acidifying agents, non-limiting examples include the mineral or organic acids such as hydrochloric acid, orthophosphoric acid, sulphuric acid, carboxylic acids such as acetic acid, tartaric acid, citric acid, lactic acid, and sulphonic acids.

Usually, the pH of the oxidizing composition (B), when it is aqueous, is below 7.

The oxidizing composition (B) can also comprise other ingredients used conventionally in this field, such as those detailed previously with reference to the anhydrous composition (A), for example fats.

Finally, the oxidizing composition (B) can be in various forms, for example a solution, an emulsion or a gel.

The method according to the disclosure is carried out in the presence of a composition (C) comprising at least one oxidation dye and/or at least one direct dye, when it is a method of coloring.

The oxidation dyes are generally chosen from the oxidation bases, optionally combined with at least one coupler.

For example, the oxidation bases can be chosen from the paraphenylenediamines, the bis-phenylalkylenediamines, the para-aminophenols, the ortho-aminophenols, the heterocyclic bases and their salts of addition.

Among the paraphenylenediamines, non-limiting examples include paraphenylenediamine, paratoluoylenediamine, 2-chloro paraphenylenediamine, 2,3 dimethyl paraphenylenediamine, 2,6-dimethyl paraphenylenediamine, 2,6-diethyl paraphenylenediamine, 2,5-dimethyl paraphenylenediamine, N,N-dimethyl paraphenylenediamine, N,N-diethyl paraphenylenediamine, N,N-dipropyl paraphenylenediamine, 4-amino N,N-diethyl 3-methyl aniline, N,N-bis-(β-hydroxyethyl) paraphenylenediamine, 4-N,N-bis-(β-hydroxyethyl)amino-2-methyl aniline, 4-N,N-bis-(β-hydroxyethyl)amino-2-chloro aniline, 2-β-hydroxyethyl paraphenylenediamine, 2-fluoro paraphenylenediamine, 2-isopropyl paraphenylenediamine, N-(β-hydroxypropyl) paraphenylenediamine, 2-hydroxymethyl paraphenylenediamine, N,N-dimethyl 3-methyl paraphenylenediamine, N,N-(ethyl,β-hydroxyethyl) paraphenylenediamine, N-(β,γ-dihydroxypropyl)paraphenylenediamine, N-(4'-aminophenyl) paraphenylenediamine, N-phenyl paraphenylenediamine, 2-β-hydroxyethyloxy paraphenylenediamine, 2-β-acetylaminoethyloxy paraphenylenediamine, N-(β-methoxyethyl) paraphenylenediamine, 4-aminophenylpyrrolidine, 2-thienyl paraphenylenediamine, 2-β-hydroxyethylamino-5-amino toluene, 3-hydroxy 1-(4'-aminophenyl)pyrrolidine and their salts of addition with an acid.

Among the paraphenylenediamines mentioned above, paraphenylenediamine, paratoluoylenediamine, 2-isopropyl paraphenylenediamine, 2-β-hydroxyethyl paraphenylenediamine, 2-β-hydroxyethyloxy paraphenylenediamine, 2,6-dimethyl paraphenylenediamine, 2,6-diethyl paraphenylenediamine, 2,3-dimethyl paraphenylenediamine, N,N-bis-(β-hydroxyethyl) paraphenylenediamine, 2-chloro paraphenylenediamine, 2-β-acetylaminoethyloxy paraphenylenediamine, and their salts of addition with an acid may be used.

Among the bis-phenylalkylenediamines, non-limiting examples include N,N'-bis-(β-hydroxyethyl) N,N'-bis-(4'-aminophenyl) 1,3-diamino propanol, N,N'-bis-(β-hydroxyethyl) N,N'-bis-(4'-aminophenyl)ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl) tetramethylenediamine, N,N'-bis-(ethyl) N,N'-bis-(4'-amino, 3'-methylphenyl)ethylenediamine, 1,8-bis-(2,5-diamino phenoxy)-3,6-dioxaoctane, and their salts of addition.

Among the para-aminophenols, non-limiting examples include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl aminomethyl)phenol, 4-amino-2-fluorophenol, and their salts of addition with an acid.

Among the ortho-aminophenols, non-limiting examples include 2-aminophenol, 2-amino-5-methylphenol, 2-amino-6-methylphenol, 5-acetamido 2-aminophenol, and their salts of addition.

Among the heterocyclic bases, we may mention, as examples, the pyridine derivatives, the pyrimidine derivatives and the pyrazole derivatives.

Among the pyridine derivatives, non-limiting examples include the compounds described for example in patents GB 1 026 978 and GB 1 153 196, such as 2,5-diamino pyridine, 2-(4-methoxyphenyl)amino-3-amino pyridine, 3,4-diamino pyridine, and their salts of addition.

Other pyridine oxidation bases that can be used in the present disclosure include the 3-amino pyrazolo[1,5-a]pyridine oxidation bases or their salts of addition described for example in patent application FR 2801308. Non-limiting examples include pyrazolo[1,5-a]pyridin-3-ylamine; 2-acetylamino pyrazolo[1,5-a]pyridin-3-ylamine; 2-morpholin-4-yl-pyrazolo[1,5-a]pyridin-3-ylamine; 3-amino-pyrazolo[1,5-a]pyridine-2-carboxylic acid; 2-methoxy-pyrazolo[1,5-a]pyridin-3-ylamino; (3-amino-pyrazolo[1,5-a]pyridin-7-yl)-methanol; 2-(3-amino-pyrazolo[1,5-a]pyridin-5-yl)ethanol; 2-(3-amino-pyrazolo[1,5-a]pyridin-7-yl)ethanol; (3-amino-pyrazolo[1,5-a]pyridin-2-yl)methanol; 3,6-diamino-pyrazolo[1,5-a]pyridine; 3,4-diamino-pyrazolo[1,5-a]pyridine; pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)amino]ethanol; 2-[(3-amino-pyrazolo[1,5-a]pyridin-7-yl)-(2-hydroxyethyl)amino]ethanol; 3-amino-pyrazolo[1,5-a]pyridin-5-ol; 3-amino-pyrazolo[1,5-a]pyridin-4-ol; 3-amino-pyrazolo[1,5-a]pyridin-6-ol; 3-amino-pyrazolo[1,5-a]pyridin-7-ol; as well as their salts of addition.

Among the pyrimidine derivatives, non-limiting examples include the compounds described for example in patents DE 2359399; JP 88-169571; JP 05-63124; EP 0770375 or patent application WO 96/15765 such as 2,4,5,6-tetra-aminopyrimidine, 4-hydroxy 2,5,6-triaminopyrimidine, 2-hydroxy 4,5,6-triaminopyrimidine, 2,4-dihydroxy 5,6-diaminopyrimidine, 2,5,6-triaminopyrimidine and their salts of addition and their tautomeric forms, when there is tautomeric equilibrium.

Among the pyrazole derivatives, non-limiting examples include the compounds described in patents DE 3843892, DE 4133957 and patent applications WO 94/08969, WO 94/08970, FR-A-2 733 749 and DE 195 43 988 such as 4,5-diamino 1-methylpyrazole, 4,5-diamino 1-(3-hydroxyethyl)pyrazole, 3,4-diamino pyrazole, 4,5-diamino 1-(4'-chlorobenzyl)pyrazole, 4,5-diamino 1,3-dimethylpyrazole, 4,5-diamino-3-methyl 1-phenyl pyrazole, 4,5-diamino 1-methyl 3-phenyl pyrazole, 4-amino 1,3-dimethyl 5-hydrazino pyrazole, 1-benzyl 4,5-diamino-3-methylpyrazole, 4,5-diamino-3-tert-butyl 1-methylpyrazole, 4,5-diamino 1-tert-butyl 3-methylpyrazole, 4,5-diamino 1-(β-hydroxyethyl) 3-methylpyrazole, 4,5-diamino 1-ethyl 3-methylpyrazole, 4,5-diamino 1-ethyl 3-(4'-methoxyphenyl)pyrazole, 4,5-diamino 1-ethyl 3-hydroxymethylpyrazole, 4,5-diamino-3-hydroxymethyl 1-methylpyrazole, 4,5-diamino-3-hydroxymethyl 1-isopropyl pyrazole, 4,5-diamino-3-methyl 1-isopropyl pyrazole, 4-amino-5-(2'-aminoethyl)amino 1,3-dimethyl pyrazole, 3,4,5-triamino pyrazole, 1-methyl 3,4,5-triamino pyrazole, 3,5-diamino 1-methyl 4-methylamino pyrazole, 3,5-diamino 4-(β-hydroxyethyl)amino 1-methylpyrazole, and their salts of addition. 4,5-Diamino 1-(3-methoxyethyl) pyrazole can also be used.

A 4,5-diaminopyrazole may be used, such as 4,5-diamino-1-(β-hydroxyethyl)pyrazole and/or a salt thereof.

As pyrazole derivatives, non-limiting examples include the diamino-N,N-dihydropyrazolopyrazolones such as those described in application FR-A-2 886 136 such as the following compounds and their salts of addition: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydro-pyrazol-3-one, 4,5-diamino-1,2-diethyl-1,2-dihydro-pyrazol-3-one, 4,5-diamino-1,2-di(2-hydroxyethyl)-1,2-dihydro-pyrazol-3-one, 2-amino-3-(2-hydroxyethyl)amino-6,7-dihydro-1H,5H-pyrazolo[1,2-a]pyrazol-1-one, 2-amino-3-dimethylamino-6, 7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydro-pyrazol-3-one, 4-amino-5-(3-dimethylamino-pyrrolidin-1-yl)-1,2-diethyl-1,2-dihydro-pyrazol-3-one, 2,3-diamino-6-hydroxy-6,7-dihydro-1H,5H-pyrazolo[1,2-a]pyrazol-1-one.

In certain embodiments, 2,3-diamino-6,7-dihydro-1H,5H-pyrazolo[1,2-a]pyrazol-1-one and/or a salt thereof may be used as the pyrazole derivative.

As heterocyclic bases, 4,5-diamino-1-(β-hydroxyethyl) pyrazole and/or 2,3-diamino-6,7-dihydro-1H,5H-pyrazolo[1,2-a]pyrazol-1-one and/or a salt thereof may be used.

The composition according to the disclosure can optionally comprise at least one coupler chosen from those conventionally used for the dyeing of keratin fibers.

Among these couplers, non-limiting examples include meta-phenylenediamines, meta-aminophenols, meta-diphenols, naphthalenic couplers, heterocyclic couplers as well as their salts of addition.

Suitable examples include 1,3-dihydroxy benzene, 1,3-dihydroxy 2-methyl benzene, 4-chloro 1,3-dihydroxy benzene, 2,4-diamino 1-(β-hydroxyethyloxy)benzene, 2-amino 4-(β3-hydroxyethylamino) 1-methoxybenzene, 1,3-diamino benzene, 1,3-bis-(2,4-diaminophenoxy) propane, 3-ureido aniline, 3-ureido 1-dimethylamino benzene, sesamol, 1-β-hydroxyethylamino-3,4-methylenedioxybenzene, α-naphthol, 2-methyl-1-naphthol, 6-hydroxy indole, 4-hydroxy indole, 4-hydroxy N-methyl indole, 2-amino-3-hydroxy pyridine, 6-hydroxy benzomorpholine 3,5-diamino-2,6-dimethoxypyridine, 1-N-(β-hydroxyethyl)amino-3,4-methylene dioxybenzene, 2,6-bis-(β-hydroxyethylamino)toluene, 6-hydroxy indoline, 2,6-dihydroxy 4-methylpyridine, 1-H 3-methylpyrazol-5-one, 1-phenyl 3-methylpyrazol-5-one, 2,6-dimethyl pyrazolo[1,5-b]-1,2,4-triazole, 2,6-dimethyl[3, 2-c]-1,2,4-triazole, 6-methyl pyrazolo[1,5-a]benzimidazole, their salts of addition with an acid, and mixtures thereof.

In general, the salts of addition of the oxidation bases and of the couplers that can be used within the scope of the disclosure may be chosen from the salts of addition with an acid, such as the hydrochlorides, hydrobromides, sulphates, citrates, succinates, tartrates, lactates, tosylates, benzenesulphonates, phosphates and acetates.

The oxidation base may be present in an amount ranging from 0.0001 to 10 wt. % relative to the total weight of the composition, such as ranging from 0.005 to 5 wt. %.

The content of coupler, if present, may range from 0.0001 to 10 wt. % relative to the total weight of the composition, such as ranging from 0.005 to 5 wt. %.

With regard to direct dyes, the dyes may be chosen from the ionic or nonionic species, such as cationic or nonionic.

Examples of suitable direct dyes include azo; methine; carbonyl; azine; (hetero)aryl nitro; tri(hetero)aryl methane direct dyes; porphyrins; phthalocyanins and natural direct dyes, alone or mixed.

The azo dyes may comprise a function —N═N—, whose two nitrogen atoms are not inserted in a ring simultaneously. However, insertion of one of the two nitrogen atoms of the —N═N— chain in a ring is not excluded.

The dyes of the methine class are possibly compounds comprising at least one chain chosen from >C═C< and —N═C<, the two atoms of which are not inserted in a ring simultaneously. It is specified, however, that one of the nitrogen or carbon atoms of the chains can be inserted in a ring. For example, the dyes of this family are derived from compounds such as methine, azomethine, mono- and di-arylmethane, indoamines (or diphenylamines), indophenols, indoanilines, carbocyanins, azacarbocyanins and their isomers, diazacarbocyanins and their isomers, tetraazacarbocyanins, hemicyanins.

Regarding the dyes of the carbonyl class, non-limiting examples include the dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, thioindigo, naphthalimide, anthrapyrimidine, diketopyrrolopyrrole, coumarin.

Regarding the dyes of the cyclic azine class, non-limiting examples include azine, xanthene, thioxanthene, fluorindine, acridine, (di)oxazine, (di)thiazine, pyronine.

The (hetero)aromatic nitro dyes may be chosen from benzene nitro or pyridine nitro direct dyes.

Regarding the dyes of the porphyrin or phthalocyanin type, cationic or non-cationic compounds can be used, optionally comprising at least one metal or metal ion, for example alkali and alkaline-earth metals, zinc, and silicon.

Examples of suitable direct dyes include the nitro dyes of the benzene series; the azo; azomethine; methine direct dyes; the azacarbocyanins such as the tetraazacarbocyanins (tetraazapentamethines); the quinone such as anthraquinone, naphthoquinone or benzoquinone direct dyes; the azine; xanthene; triarylmethane; indoamine; indigoid; phthalocyanin, porphyrin direct dyes, and the natural direct dyes, alone or mixed.

These dyes can be monochromophoric dyes (i.e. comprising just one colorant) or polychromophoric, for example di- or trichromophoric; the chromophores can be identical or different, and may or may not be in the same chemical family. As disclosed herein, a polychromophoric dye comprises several radicals derived from a molecule absorbent in the visible region between 400 and 800 nm. Moreover, this absorbance of the dye requires neither prior oxidation of the latter, nor combination with other chemical species.

In the case of polychromophoric dyes, the chromophores are joined together by at least one linkage, which can be cationic or non-cationic.

The linkage can be, for example, a linear, branched or cyclic $C_1$-$C_{20}$ alkyl chain, optionally interrupted by at least one heteroatom (such as nitrogen, oxygen) and/or by at least one group comprising same (CO, $SO_2$), optionally interrupted by at least one heterocycle, uncondensed or condensed with a phenyl nucleus and comprising at least one quaternized nitrogen atom inserted in said ring and optionally at least one other heteroatom (such as oxygen, nitrogen or sulphur), optionally interrupted by at least one substituted or unsubstituted phenyl or naphthyl group, optionally at least one quaternary ammonium group substituted with two, optionally substituted, $C_1$-$C_{15}$ alkyl groups; and the linkage does not comprise a nitro, nitroso, or peroxo group.

If the heterocycles or aromatic nuclei are substituted, they can be substituted for example with at least one $C_1$-$C_8$ alkyl radicals optionally substituted with a hydroxyl, $C_1$-$C_2$ alkoxy, $C_2$-$C_4$ hydroxyalkoxy, acetylamino, or amino group substituted with one or two $C_1$-$C_4$ alkyl radicals, optionally bearing at least one hydroxyl group or the two radicals can form, with the nitrogen atom to which they are attached, a heterocycle with 5 or 6 ring members, optionally comprising another heteroatom identical to or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two $C_1$-$C_4$ alkyl radicals, which may be identical or different, optionally bearing at least one hydroxyl group.

Among the benzene direct dyes usable according to the disclosure, non-limiting examples include the following compounds:
1,4-diamino-2-nitrobenzene,
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo, azomethine, methine or tetraazapentamethine direct dyes usable according to the disclosure, non-limiting examples include the cationic dyes described in patent applications WO 95/15144, WO 95/01772 and EP 714954; FR 2189006, FR 2285851, FR-2140205, EP 1378544, EP 1674073.

Suitable examples include the following dyes of formulae (I) to (IV):

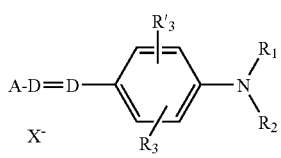

(I)

in which:
D represents a nitrogen atom or the —CH group,
$R_1$ and $R_2$, which may be identical or different, represent a hydrogen atom; a $C_1$-$C_4$ alkyl radical, which can be substituted with a —CN, —OH or —NH$_2$ radical or forms, with a carbon atom of the benzene ring, a heterocycle optionally oxygen-comprising or nitrogen-comprising, which can be substituted with at least one $C_1$-$C_4$ alkyl radicals; a 4'-aminophenyl radical, $R_3$ and $R'_3$, which may be identical or different, represent a hydrogen atom or a halogen atom chosen from chlorine, bromine, iodine, and fluorine, a cyano, $C_1$-$C_4$ alkyl, $C_1$-$C_4$ alkoxy, or acetyloxy radical, X⁻ represents an anion such as an anion chosen from chloride, methyl sulphate and acetate, A represents a group chosen from the following structures $A_1$ to $A_{18}$:

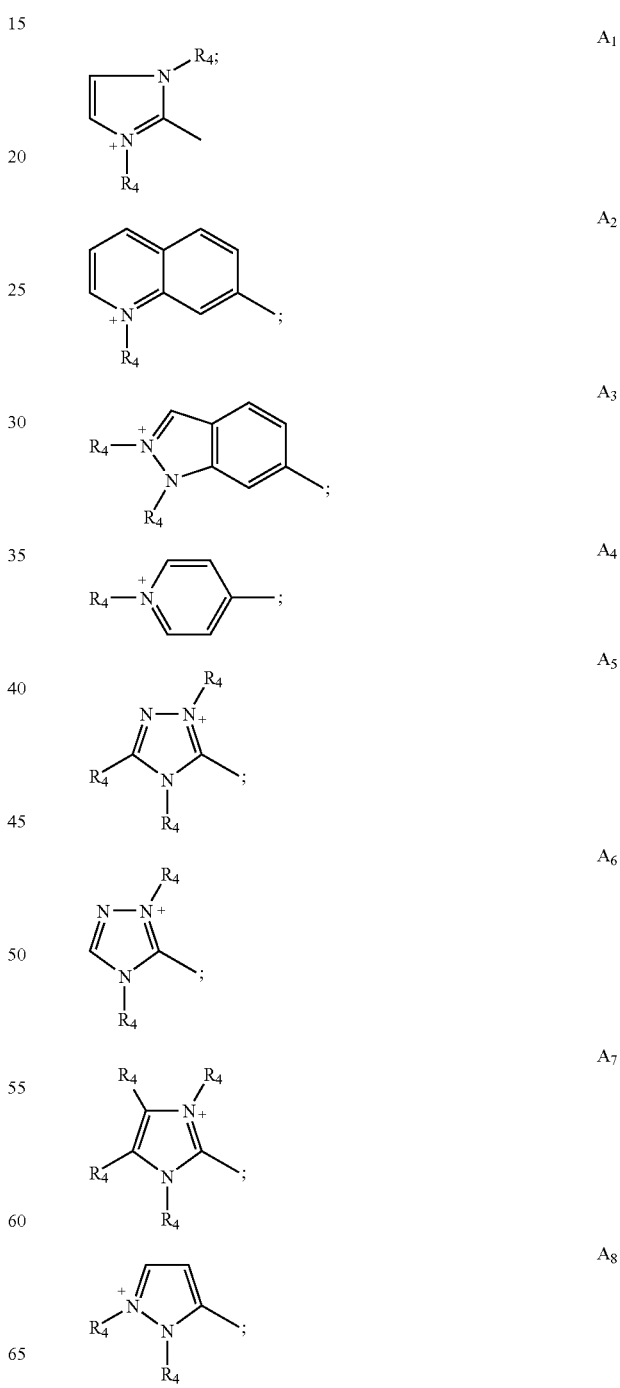

-continued

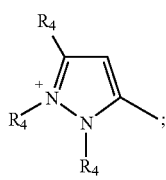

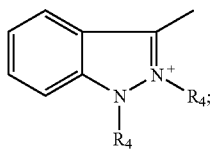

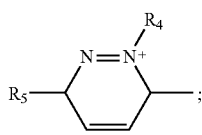

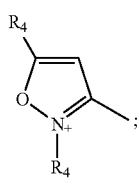

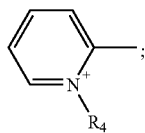

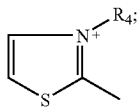

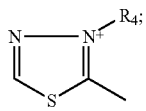

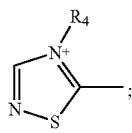

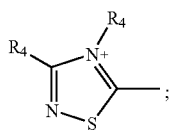

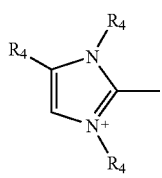

in which $R_4$ represents a $C_1$-$C_4$ alkyl radical, which can be substituted with a hydroxyl radical, and $R_5$ represents a $C_1$-$C_4$ alkoxy radical;

$A_9$ $A_{10}$ $A_{11}$ $A_{12}$ $A_{13}$ $A_{14}$ $A_{15}$ $A_{16}$ $A_{17}$ $A_{18}$

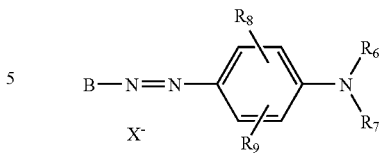 (II)

in which:

$R_6$ represents a hydrogen atom or a $C_1$-$C_4$ alkyl radical, $R_7$ represents a hydrogen atom, an alkyl radical which can be substituted with a —CN radical or with an amino group, a 4'-aminophenyl radical or forms with $R_6$ a heterocycle, optionally oxygen-comprising and/or nitrogen-comprising which can be substituted with a $C_1$-$C_4$ alkyl radical, $R_8$ and $R_9$, which may be identical or different, represent a hydrogen atom, a halogen atom such as bromine, chlorine, iodine or fluorine, a $C_1$-$C_4$ alkyl or $C_1$-$C_4$ alkoxy radical, a —CN radical, $X^-$ represents an anion, such as an anion chosen from chloride, methyl sulphate, and acetate, B represents a group chosen from the following structures $B_1$ to $B_6$:

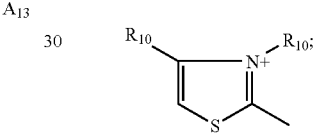 B1

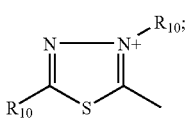 B2

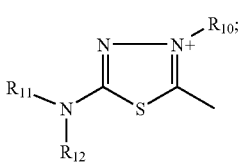 B3

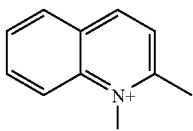 B4

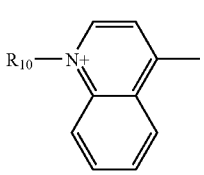 B5

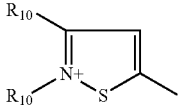 B6 in which $R_{10}$ represents a $C_1$-$C_4$ alkyl radical, $R_{11}$ and $R_{12}$, which may be identical or different, represent a hydrogen atom or a $C_1$-$C_4$ alkyl radical;

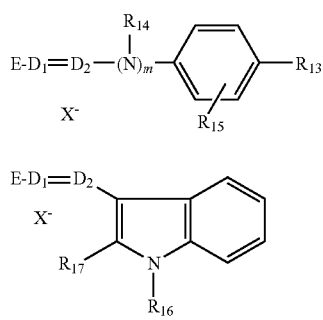 (III)

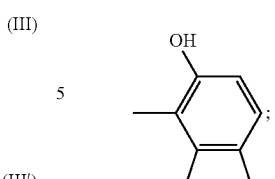 E5

(III')

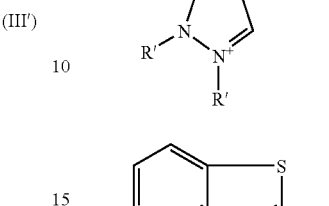 E6 in which:

$R_{13}$ represents a hydrogen atom, a $C_1$-$C_4$ alkoxy radical, a halogen atom such as bromine, chlorine, iodine, or fluorine, $R_{14}$ represents a hydrogen atom, a $C_1$-$C_4$ alkyl radical or forms, with a carbon atom of the benzene ring, a heterocycle optionally oxygen-comprising and/or substituted with at least one $C_1$-$C_4$ alkyl group, $R_{15}$ represents a hydrogen atom or a halogen atom such as bromine, chlorine, iodine or fluorine, $R_{16}$ and $R_{17}$, which may be identical or different, represent a hydrogen atom or a $C_1$-$C_4$ alkyl radical, $D_1$ and $D_2$, which may be identical or different, represent a nitrogen atom or the —CH group, m=0 or 1, such as 1, it being understood that when $R_{13}$ represents an unsubstituted amino group, $D_1$ and $D_2$ represent simultaneously a —CH group and m=0, $X^-$ represents an anion such as an anion chosen from chloride, methyl sulphate, and acetate, E represents a group chosen from the following structures $E_1$ to $E_8$, such as $E_1$, $E_2$, and $E_7$:

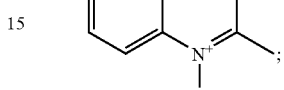 E7 and

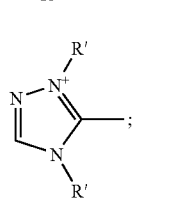 E8 in which R' represents a $C_1$-$C_4$ alkyl radical;

when m=0 and $D_1$ represents a nitrogen atom, E can also represent a group with the following structure $E_9$:

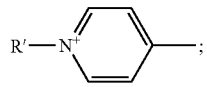 E1

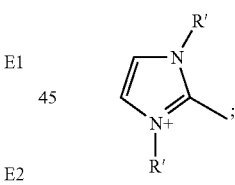 E9

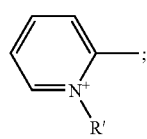 E2 in which R' represents a $C_1$-$C_4$ alkyl radical.

G-N=N-J    (IV)

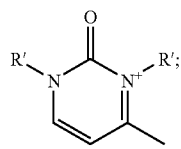 E3 in which:

the symbol G represents a group chosen from the following structures $G_1$ to $G_3$:

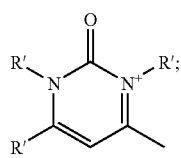 E4

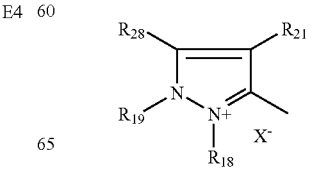 $G_1$

-continued

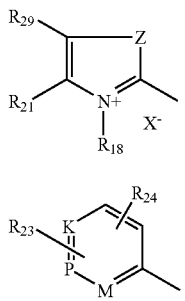

in which structures $G_1$ to $G_3$, $R_{18}$ represents a $C_1$-$C_4$ alkyl radical, a phenyl radical which can be substituted with a $C_1$-$C_4$ alkyl radical or a halogen atom chosen from chlorine, bromine, iodine, and fluorine;

$R_{19}$ represents a $C_1$-$C_4$ alkyl radical or a phenyl radical;

$R_{20}$ and $R_{21}$, which may be identical or different, represent a $C_1$-$C_4$ alkyl radical, a phenyl radical, or form together in $G_1$ a benzene ring substituted with at least one $C_1$-$C_4$ alkyl, $C_1$-$C_4$ alkoxy, or $NO_2$ radicals, or form together in $G_2$ a benzene ring optionally substituted with at least one $C_1$-$C_4$ alkyl, $C_1$-$C_4$ alkoxy, or $NO_2$ radicals;

$R_{20}$ can in addition represent a hydrogen atom;

Z represents an oxygen atom, a sulphur atom, or a group —$NR_{19}$;

M represents a —CH, —CR group (R represents $C_1$-$C_4$ alkyl), or —$NR_{22}(X^-)_r$;

K represents a —CH, —CR group (R represents $C_1$-$C_4$ alkyl), or —$NR_{22}(X^-)_r$;

P represents a —CH, —CR group (R represents $C_1$-$C_4$ alkyl), or —$NR_{22}(X^-)_r$; r represents zero or 1;

$R_{22}$ represents an atom $O^-$, a $C_1$-$C_4$ alkoxy radical, or a $C_1$-$C_4$ alkyl radical;

$R_{23}$ and $R_{24}$, which may be identical or different, represent a hydrogen atom or a halogen atom chosen from chlorine, bromine, iodine and fluorine, a $C_1$-$C_4$ alkyl, $C_1$-$C_4$ alkoxy radical, a radical —$NO_2$;

$X^-$ represents an anion such as an anion chosen from chloride, iodide, methyl sulphate, ethyl sulphate, acetate, and perchlorate;

provided that, if $R_{22}$ represents $O^-$, then r represents zero;

if K or P or M represents —N-alkyl $C_1$-$C_4 X^-$, then $R_{23}$ or $R_{24}$ may be different from a hydrogen atom;

if K represents —$NR_{22}(X^-)_r$, then M=P=—CH, —CR;

if M represents —$NR_{22}(X^-)_r$, then K=P=—CH, —CR;

if P represents —$NR_{22}(X^-)_r$, then K=M and they represent —CH or —CR;

if Z represents a sulphur atom with $R_{21}$ representing $C_1$-$C_4$ alkyl, then $R_{20}$ is different from a hydrogen atom;

if Z represents —$NR_{22}$ with $R_{19}$ representing $C_1$-$C_4$ alkyl, then at least one of the radicals $R_{18}$, $R_{20}$ or $R_{21}$ of the group of structure $G_2$ is different from a $C_1$-$C_4$ alkyl radical; the symbol J represents:

(a) a group with the following structure $J_1$:

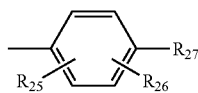

in which structure $J_1$, $R_{25}$ represents a hydrogen atom, a halogen atom chosen from chlorine, bromine, iodine, and fluorine, a $C_1$-$C_4$ alkyl radical, $C_1$-$C_4$ alkoxy, an —OH, —$NO_2$, —$NHR_{28}$, —$NR_{29}R_{30}$, $C_1$-$C_4$—NHCOalkyl radical, or forms with $R_{26}$ a 5- or 6-membered ring comprising or not comprising at least one heteroatoms chosen from nitrogen, oxygen, or sulphur;

$R_{26}$ represents a hydrogen atom, a halogen atom chosen from chlorine, bromine, iodine, and fluorine, a $C_1$-$C_4$ alkyl, $C_1$-$C_4$ alkoxy radical, or forms with $R_{27}$ or $R_{28}$ a 5- or 6-membered ring comprising or not comprising at least one heteroatom chosen from nitrogen, oxygen, or sulphur;

$R_{27}$ represents a hydrogen atom, a radical —OH, a radical —$NHR_{28}$, a radical —$NR_{29}R_{30}$;

$R_{28}$ represents a hydrogen atom, a $C_1$-$C_4$ alkyl radical, a $C_1$-$C_4$ monohydroxyalkyl radical, $C_2$-$C_4$ polyhydroxyalkyl radical, a phenyl radical;

$R_{29}$ and $R_{30}$, which may be identical or different, represent a $C_1$-$C_4$ alkyl radical, a $C_1$-$C_4$ monohydroxyalkyl radical, $C_2$-$C_4$ polyhydroxyalkyl radical;

(b) a nitrogen-comprising heterocyclic group with 5 or 6 ring members which may comprise other heteroatoms and/or carbonyl groups and can be substituted with at least one $C_1$-$C_4$ alkyl, amino or phenyl radicals, and a group with the following structure $J_2$:

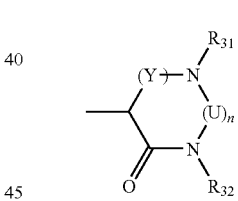

in which structure $J_2$, $R_{31}$ and $R_{32}$, which may be identical or different, represent a hydrogen atom, a $C_1$-$C_4$ alkyl radical, a phenyl radical;

Y represents the radical —CO— or the radical

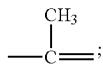

n=0 or 1, and when n represents 1, U represents the radical —CO—.

In structures (I) to (IV) defined above, the $C_1$-$C_4$ alkyl or alkoxy group such as methyl, ethyl, butyl, methoxy, ethoxy.

In certain embodiments, A represents a group chosen from the following structures $A_1$, $A_4$, $A_7$, $A_{13}$, and $A_{18}$.

In certain embodiments, the compounds of formulae (I) and (III) are used. Among the compounds of formulae (I) and (III), the following compounds may be used:

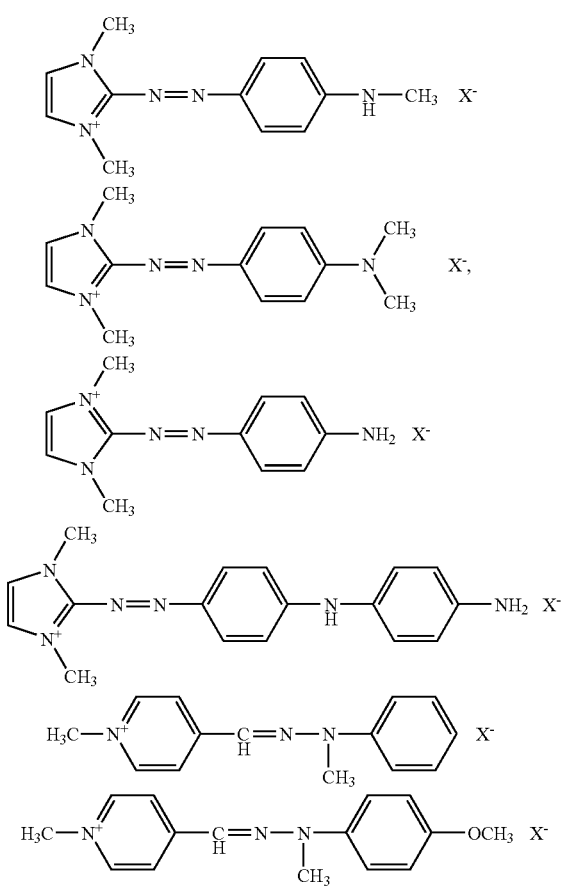

Suitable azo direct dyes include the following dyes described in the COLOR INDEX INTERNATIONAL 3rd edition:
Disperse Red 17
Basic Red 22
Basic Red 76
Basic Yellow 57
Basic Brown 16
Basic Brown 17
Disperse Black 9.

Suitable azo direct dyes also include 1-(4'-aminodiphenylazo)-2-methyl-4-bis(β-hydroxyethyl)aminobenzene.

Among the quinone direct dyes, the following dyes are non-limiting examples:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99
as well as the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes, the following compounds are non-limiting examples:
Basic Blue 17
Basic Red 2.

Among the triarylmethane dyes usable according to the disclosure, the following compounds are non-limiting examples:
Basic Green 1
Basic Violet 3
Basic Violet 14
Basic Blue 7
Basic Blue 26

Among the indoamine dyes usable according to the disclosure, the following compounds are non-limiting examples:
2-β-hydroxyethlyamino-5[bis(β-4'-hydroxyethyl)amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl,carbamylmethyl)amino]phenyl-ureido-6-methyl-1,4-benzoquinone imine.

Among the dyes of the tetraazapentamethine type usable according to the disclosure, the compounds shown in the following table are non-limiting examples:

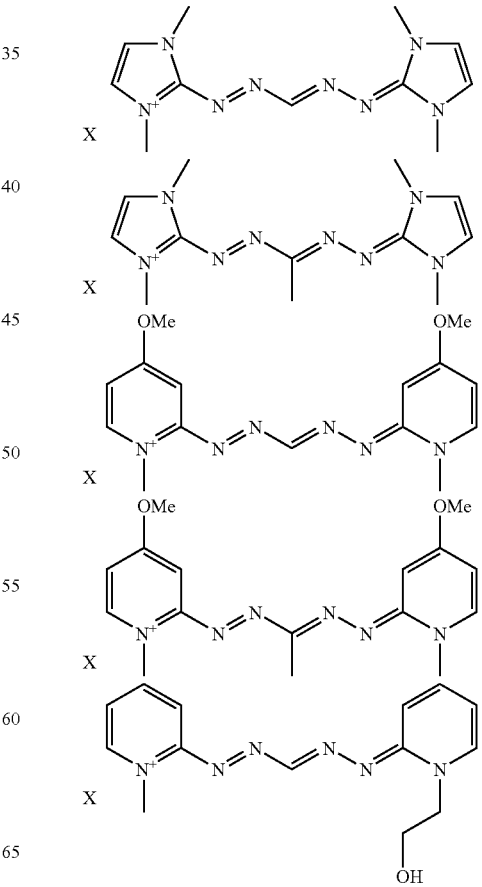

-continued

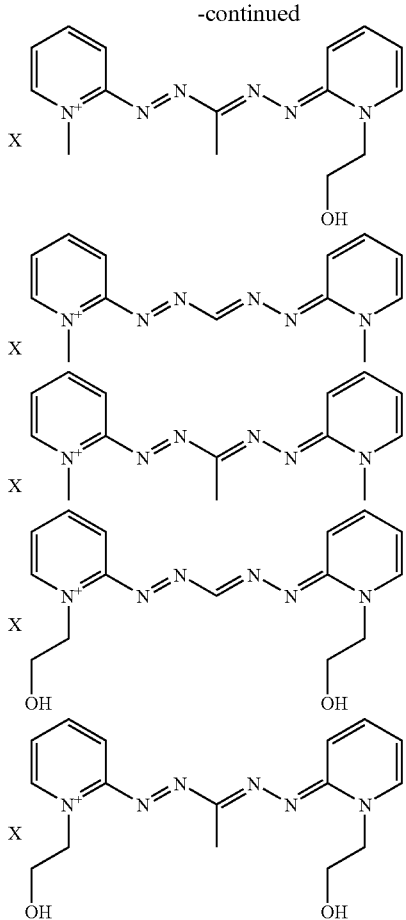

$X^-$ represents an anion, such as an anion chosen from chloride, iodide, methyl sulphate, ethyl sulphate, acetate, and perchlorate.

Among the polychromophoric dyes, non-limiting examples include the di- or trichromophoric azo and/or azomethine (hydrazone) dyes, symmetrical or unsymmetrical, comprising on the one hand at least one aromatic heterocycle with 5 or 6 ring members, optionally condensed, comprising at least one quaternized nitrogen atom inserted in said heterocycle and optionally at least one other heteroatom (such as nitrogen, sulphur, oxygen), and on the other hand, at least one phenyl or naphthyl group, optionally substituted, optionally bearing at least one group OR with R representing a hydrogen atom, an optionally substituted $C_1$-$C_6$ alkyl radical, an optionally substituted phenyl nucleus, or at least one group $N(R')_2$ with R', identical or different, representing a hydrogen atom, an optionally substituted $C_1$-$C_6$ alkyl radical, an optionally substituted phenyl nucleus; and the radicals R' can form, with the nitrogen atom to which they are bound, a saturated heterocycle with 5 or 6 ring members, or alternatively one and/or both radicals R' can each form, with the carbon atom of the aromatic ring positioned ortho to the nitrogen atom, a saturated heterocycle with 5 or 6 ring members.

As cationic aromatic heterocycle, non-limiting examples include the rings with 5 or 6 ring members comprising 1 to 3 nitrogen atoms, such as 1 or 2 nitrogen atoms, one being quaternized; said heterocycle moreover optionally being condensed with a benzene ring. It should also be noted that the heterocycle can optionally comprise another heteroatom different from nitrogen, such as sulphur or oxygen.

If the heterocycles or phenyl or naphthyl groups are substituted, they are substituted for example with at least one $C_1$-$C_8$ alkyl radicals optionally substituted with a hydroxy, $C_1$-$C_2$ alkoxy, $C_2$-$C_4$ hydroxyalkoxy, acetylamino, amino group substituted with one or two $C_1$-$C_4$ alkyl radicals, optionally bearing at least one hydroxyl group or the two radicals can form, with the nitrogen atom to which they are attached, a heterocycle with 5 or 6 ring members, optionally comprising another heteroatom, identical or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two $C_1$-$C_4$ alkyl radicals, which may be identical or different, optionally bearing at least one hydroxyl group.

These polychromophores can be joined together by at least one linkage optionally comprising at least one quaternized nitrogen atom, which may or may not be inserted in a saturated or unsaturated, optionally aromatic heterocycle.

The linkage may be linear, branched or cyclic $C_1$-$C_{20}$ alkyl chain, optionally interrupted by at least one heteroatom (such as nitrogen, oxygen) and/or by at least one group comprising same (CO, $SO_2$), optionally interrupted by at least one heterocycle condensed or not with a phenyl nucleus and comprising at least one quaternized nitrogen atom inserted in said ring and optionally at least one other heteroatom (such as oxygen, nitrogen, or sulphur), optionally interrupted by at least one substituted or unsubstituted phenyl or naphthyl group, optionally at least one quaternary ammonium group substituted with two optionally substituted $C_1$-$C_{15}$ alkyl groups; and the linkage does not comprise a nitro, nitroso, or peroxo group.

The bond between the linkage and each chromophore is generally made by means of a heteroatom substituting the phenyl or naphthyl nucleus or by means of the quaternized nitrogen atom of the cationic heterocycle.

The dye can comprise identical or different chromophores.

Examples of such dyes can be found in patent applications EP 1637566, EP 1619221, EP 1634926, EP 1619220, EP 1672033, EP 1671954, EP 1671955, EP 1679312, EP 1671951, EP167952, EP167971, WO 06/063866, WO 06/063867, WO 06/063868, WO 06/063869, EP 1408919, EP 1377264, EP 1377262, EP 1377261, EP 1377263, EP 1399425, EP 1399117, EP 1416909, EP 1399116, and EP 1671560.

It is also possible to use cationic direct dyes as mentioned in applications EP 1006153, which describes dyes comprising two chromophores of the anthraquinone type joined by a cationic linkage; EP 1433472, EP 1433474, EP 1433471 and EP 1433473 which describe identical or different dichromophoric dyes, joined by a cationic or non-cationic linkage, as well as EP 6291333 which may describe dyes comprising three chromophores, one of which is an anthraquinone chromophore, to which two chromophores of the azo or diazacarbocyanin type or an isomer thereof are joined.

Among the natural direct dyes usable according to the disclosure, non-limiting examples include lawsone, juglone, alizarin, purpurine, carminic acid, kermesic acid, purpurogallin, protocatechaldehyde, indigo, isatin, curcumin, spinulosin, apigenidin, orceins. Extracts or decoctions comprising these natural dyes, and cataplasms or extracts based on henna, can also be used.

When present, the amount of direct dye may range from 0.0001 to 10 wt. % of the total weight of the composition, for example an amount ranging from 0.005 to 5 wt. %.

Composition (C) can comprise at least one and/or the other types of dyes. It can optionally be derived from a mixture of two dyeing compositions, one comprising the at least one oxidation dye, the other the at least one direct dye.

Another ingredient of composition (C) is represented by at least one inorganic base.

Inorganic compound means, in the sense of the present disclosure, any compound having in its structure at least one element from columns 1 to 13 of the periodic table of the elements other than hydrogen, not comprising at least one atom of carbon and of hydrogen simultaneously.

According to one embodiment of the disclosure, the inorganic base comprises at least one element from columns 1 and 2 of the periodic table of the elements other than hydrogen.

As a possible variant the inorganic base has the following structure:

$$(Z_1^{x-})_m(Z_2^{y+})_n$$

in which $Z_2$ represents a metal from columns 1 to 13 of the periodic table of the elements, such as 1 or 2, such as sodium or potassium;

$Z_1^{x-}$ represents an anion chosen from the ions $CO_3^{2-}$, $OH^-$, $HCO_3^{2-}$, $SiO_3^{2-}$, $HPO_4^{2-}$, $PO_4^{3-}$, $B_4O_7^{2-}$, such as from the ions $CO_3^{2-}$, $OH^-$, $SiO_3^{2-}$;

x represents 1, 2 or 3;

y represents 1, 2, 3 or 4;

m and n represent independently of one another 1, 2, 3, or 4;

with (n)(y)=(m)(x).

The inorganic base may correspond to the following formula $(Z_1^-)_m(Z_2^{y+})_n$, in which $Z_2$ represents a metal from columns 1 and 2 of the periodic table of the elements; $Z_1^{x-}$ represents an anion chosen from the ions $CO_{32-}$, $OH_-$, $SiO_3^{2-}$, x has a value of 1, y represents 1 or 2, m and n represent independently of one another 1 or 2 with (n)(y)=(m)(x).

Non-limiting examples of the inorganic base usable according to the disclosure include sodium carbonate, potassium carbonate, sodium hydroxide, potassium hydroxide, sodium metasilicate, and potassium metasilicate. For example the inorganic base can be an alkaline carbonate in certain embodiments.

Composition (C) can have a content of at least inorganic base ranging from 0.01 to 30 wt. % relative to the weight of said composition, such as a content ranging from 0.1 to 20 wt. %.

Composition (C) can also comprise at least one additional organic amine whose pKb at 25° C. is less than 12, such as less than 10, or less than 6.

The organic amines of the following formula may be suitable:

$$\begin{array}{c} Rx \\ \phantom{Rx} \diagdown \\ \phantom{Rxx} N-W-N \\ \phantom{Rxxx} \diagup \phantom{W} \diagdown \\ Ry \phantom{xxxxxxx} Rt \end{array} \begin{array}{c} Rz \\ \diagup \end{array}$$

in which W is a $C_1$-$C_6$ alkylene residue optionally substituted with a hydroxyl group or a $C_1$-$C_6$ alkyl radical; Rx, and Ry, Rz and Rt, which may be identical or different, represent a hydrogen atom, a $C_1$-$C_6$ alkyl radical or $C_1$-$C_6$ hydroxyalkyl, $C_1$-$C_6$ aminoalkyl.

Examples of such amines include 1,3-diaminopropane, 1,3-diamino-2-propanol, spermine, spermidine.

According to a second variant, the organic amine can be chosen from the amino acids.

For example, the amino acids that can be used are of natural or synthetic origin, in their L, D, or racemic forms and have at least one acid function which may be selected from the carboxylic, sulphonic, phosphonic, or phosphoric acid functions. The amino acids can be in neutral or ionic form.

As amino acids usable in the present disclosure, non-limiting examples include aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

The amino acids may be basic amino acids comprising a supplementary amine function optionally included in a ring or in a ureido function.

These basic amino acids may be chosen from those corresponding to the following formula (I):

$$R-CH_2-CH \begin{array}{c} NH_2 \\ \diagdown \\ \diagup \\ CO_2H \end{array} \quad (I)$$

where R represents a group chosen from:

$$\begin{array}{c} \text{imidazole ring} \end{array}; \quad -(CH_2)_3NH_2; \quad -(CH_2)_2NH_2;$$

$$-(CH_2)_2NHCONH_2; \quad \text{and} \quad -(CH_2)_2NH-\underset{\underset{NH}{\|}}{C}-NH_2;$$

The compounds corresponding to formula (I) can be histidine, lysine, arginine, ornithine, and citrulline.

According to one embodiment of the disclosure, the organic amine can be chosen from the basic amino acids. The amino acids may be arginine, lysine, and histidine, or mixtures thereof.

According to another embodiment, the organic amine can be chosen from the organic amines of the heterocyclic type. Non-limiting examples, apart from histidine already mentioned in the amino acids, include pyridine, piperidine, imidazole, triazole, tetrazole, and benzimidazole.

According to another embodiment, the organic amine is chosen from the dipeptides of amino acids. As dipeptides of amino acids usable in the present disclosure, non-limiting examples include carnosine, anserine, and baleen.

According to another embodiment of the disclosure, the organic amine is chosen from the compounds bearing a guanidine function. As amines of this type usable in the present disclosure, non-limiting examples, apart from arginine already mentioned as amino acid, include creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino (imino)methyl]amino)ethane-1-sulphonic acid.

For example, if an additional organic amine is used, it can be chosen from the basic amino acids, or monoethanolamine.

In certain embodiments, if an additional organic amine is present in composition (C), its content may range from 0.01 to 30 wt % relative to the weight of said composition, such as a content ranging from 0.1 to 20 wt. %.

Composition (C) can be an anhydrous composition or aqueous composition. An aqueous composition means a composition comprising more than 5 wt. % of water, such as comprising more than 10 wt. % of water, or compromising more than 20 wt. % of water.

In certain embodiments, composition (C) may be an aqueous composition.

The composition can optionally comprise at least one solvent. Those that were mentioned within the scope of the description of aqueous composition (B) may be suitable for composition (C), also at the stated level of concentrations.

Composition (C) can also comprise conventional additives such as those that were listed previously, to which reference can be made.

The pH of composition (C) if it is aqueous can range from 2 to 12, such as ranging from 8 to 11. The pH is adjusted using acidifying or alkalizing agents (inorganic or organic amines), such as those mentioned previously.

In certain embodiments, if the composition applied on the hair (comprising compositions (A), (B) and (C)) includes ammonia, its ammonia content may be less than or equal to 0.03 wt. % relative to the final composition (expressed as $NH_3$), such as less than or equal to 0.01 wt. % relative to the final composition. In certain embodiments, the final composition results from mixing compositions (A), (B) and (C); mixing being carried out either before application on the keratin fibers (extemporaneous preparation) or directly on the keratin fibers (successive applications with or without premixing and without intermediate rinsing).

According to an embodiment of the disclosure, compositions (A), (B) and (C) are applied on the dry or wet keratin fibers, successively and without intermediate rinsing; for example compositions (A) then (C) then (B) or (C) then (A) then (B) are applied.

Another embodiment corresponds to successive application, without intermediate rinsing, of the composition resulting from mixing, prior to application, compositions (A) and (C) and then the oxidizing composition (B).

According to another embodiment, a composition obtained by extemporaneous mixing, before application, of compositions (A), (B) and (C) is applied on the dry or wet keratin fibers.

In another embodiment, the weight ratios $R_1$ of the amounts of compositions [(A)+(C)]/(B) and $R_2$ of the amounts of compositions (A)/(C) range from 0.1 to 10, such as from 0.3 to 3.

Regardless of the variant employed, the mixture present on the fibers (resulting either from extemporaneous mixing of the compositions or from successive application of the latter) can be left in place generally for a time of the order of 1 minute to 1 hour, such as from 5 minutes to 30 minutes.

The temperature during the method conventionally ranges from room temperature (from 15 to 25° C.) to 80° C., such as from room temperature to 60° C.

At the end of the treatment, human keratin fibers are optionally rinsed with water, optionally are washed with shampoo followed by rinsing with water, before being dried or left to dry.

Another object of the disclosure relates to a kit with several compartments comprising a first compartment comprising the aforementioned anhydrous composition (A) comprising at least one fat and at least one surfactant, a second compartment comprising a composition (B) comprising at least one oxidizing agent, and a third compartment comprising a composition (C) comprising at least one inorganic base.

According to another embodiment composition (C) comprises at least one oxidation dye and/or at least one direct dye.

The following examples serve to illustrate the disclosure, though without limiting its scope.

EXAMPLE 1

The following compositions were prepared (the amounts are expressed in grams of active substance):

Composition $A_1$

| | |
|---|---|
| Ethoxylated sorbitan monolaurate (4EO) | 21.7 |
| Pyrogenic silica of hydrophobic character | 11.1 |
| Liquid paraffin | Q.s. 100 |

Composition $C_1$

| | |
|---|---|
| Potassium carbonate | 7.25 |
| Para-phenylenediamine | 2.35 |
| Resorcinol | 2.37 |
| Sodium metabisulphite | 0.70 |
| Ascorbic acid | 0.25 |
| Pentasodium pentetate | 1.00 |
| Ethanol | 8.80 |
| Propylene glycol | 6.20 |
| Hexylene glycol | 3.00 |
| Dipropylene glycol | 3.00 |
| Demineralized water | Q.s. 100 |

The following were mixed at the moment of use:
10 parts by weight of composition $A_1$
4 parts by weight of composition $C_1$
15 parts by weight of oxidant Platinium international 20 Volumes (hydrogen peroxide) (composition B)

The mixture obtained (pH=9.4) was then applied on natural locks of hair at 90% white and on permed locks at 90% white.

The bath ratio "mixture/lock of hair" was respectively 10/1 (g/g).

The waiting time was 30 minutes at 27° C.

At the end of this time, the locks of hair were rinsed, then washed with Elsève multivitamin shampoo.

No pungent odor was observed, neither during preparation of the dye mixture, nor during application on the locks of hair.

Moreover, as shown in the table given below, a strong coloration was obtained, with low selectivity.

The selectivity was calculated after measuring the coloration of the locks of hair in the CIE system l*a*b* by means of a Minolta Spectrophotometer CM2600D colorimeter.

The selectivity, designated ΔE*, was calculated from the values of L*a*b* according to the following equation:

$$\Delta E^* = \sqrt{(L^*-L_o)^2 + (a-a_o)^2 + (b-b_o^*)^2}$$

where L*, a* and b* represent the values measured on the natural locks of hair and $L_0^*$, $a_0^*$ and $b_0^*$ represent the values measured on the permed locks of hair.

The lower the value of ΔE*, the better the uniformity of the coloration obtained.

| | L* | a* | b* | ΔE* |
|---|---|---|---|---|
| Natural hair | 18.01 | 2.41 | 3.07 | 0.24 |
| Permed hair | 18.05 | 2.26 | 2.89 | |

EXAMPLE 2

The following compositions were prepared (the amounts were expressed in grams of active substance):

Composition $A_1$

| | |
|---|---|
| Ethoxylated sorbitan monolaurate (4EO) | 21.7 |
| Pyrogenic silica of hydrophobic character | 11.1 |
| Liquid paraffin | Q.s. 100 |

Composition $C_2$

| | |
|---|---|
| Potassium carbonate | 7.25 |
| Para-phenylenediamine | 2.39 |
| 4-Amino-2-hydroxytoluene | 2.68 |
| Sodium metabisulphite | 0.70 |
| Ascorbic acid | 0.25 |
| Pentasodium pentetate | 1.00 |
| Demineralized water | 64.73 |
| Ethanol | 8.80 |
| Propylene glycol | 6.20 |
| Hexylene glycol | 3.00 |
| Dipropylene glycol | 3.00 |

The following were mixed at the moment of use:
10 parts by weight of composition $A_1$,
4 parts by weight of composition $C_2$,
15 parts by weight of oxidant Platinium international 20 Volumes (hydrogen peroxide) (composition B).

The mixture obtained (pH=9.5) was then applied on natural locks of hair at 90% white and on permed locks of hair at 90% white.

The bath ratio "mixture/lock of hair" was respectively 10/1 (g/g).

The waiting time was 30 minutes at 27° C.

At the end of this time, the locks of hair were rinsed, then washed with Elsève multivitamin shampoo.

No pungent odor was observed, neither during preparation of the dye mixture, nor during application on the locks of hair.

Moreover, as shown in the following table (values and calculations obtained as in Example 1), a strong dark purple coloration was obtained, with low selectivity.

| | L* | a* | b* | ΔE* |
|---|---|---|---|---|
| Natural hair | 17.83 | 5.85 | 0.03 | 1.31 |
| Permed hair | 17.77 | 7.15 | 0.17 | |

EXAMPLE 3

The following compositions were prepared:
Composition $A_1$

| | |
|---|---|
| Ethoxylated sorbitan monolaurate (4EO) | 21.7 |
| Pyrogenic silica of hydrophobic character | 11.1 |
| Liquid paraffin | Q.s. 100 |

Composition $B_3$

| | |
|---|---|
| sodium hydroxide | 20 |
| Demineralized water | 80 |

The following were mixed at the moment of use:
9 parts by weight of composition $A_1$
1 part by weight of composition $B_3$
10 parts by weight of oxidant 20 Volumes (6% of hydrogen peroxide).

In parallel, a formula of the prior art was prepared:

| | |
|---|---|
| Oleic alcohol polyglycerolated with 2 moles of glycerol | 4 |
| Oleic alcohol polyglycerolated with 4 moles of glycerol | 5.69 AS |
| Oleic acid | 3 |
| Oleic amine at 2 moles of ethylene oxide sold under the trade name ETHOMEEN 012 by the company Akzo | 7 |
| Diethylaminopropyl laurylamino succinamate, sodium salt at 55% A.S. | 3.0 AS |
| Oleic alcohol | 5 |
| Diethanolamide of oleic acid | 12 |
| Ethanol | 7 |
| Propylene glycol | 3.5 |
| Dipropylene glycol | 0.5 |
| Monomethyl ether of propylene glycol | 9 |
| Ammonium acetate | 0.8 |
| Sodium hydroxide | 2 |
| Demineralized water q.s.f. | 100 g |

At the moment of use, the composition of the prior art was mixed weight for weight with oxidant 20 Volumes (comprising 6% of hydrogen peroxide).

The final concentration of sodium hydroxide was the same in the mixture of the disclosure as in that of the prior art, namely 1 g %. The pH values of the two mixtures were 10.9±0.2.

Each mixture was then applied on a lock of natural chestnut-colored hair (height of tone 5). The bath ratio "mixture/lock of hair" was respectively 10/1 (g/g). The holding time was 45 min at 27° C. At the end of this time, the locks of hair were rinsed, then washed with Elsève multivitamin shampoo.

The following table shows that the method according to the disclosure gives greater lightening than that of the prior art.

| | L* | a* | b* | ΔE*ab |
|---|---|---|---|---|
| Untreated hair | 20.1 | 3.3 | 3.6 | / |
| Hair treated with the mixture of the disclosure | 29.8 | 8.9 | 14.8 | 15.8 |
| Hair treated with the mixture of the prior art | 27.2 | 7.9 | 11.7 | 11.7 |

EXAMPLE 4

The following compositions were prepared:
Composition $A_1$

| | |
|---|---|
| Ethoxylated sorbitan monolaurate (4EO) | 21.7 |
| Pyrogenic silica with hydrophobic character | 11.1 |
| Liquid paraffin | Q.s. 100 |

Composition $B_4$

| | |
|---|---|
| Potassium carbonate | 20 |
| Demineralized water | 80 |

The following were mixed at the moment of use:
9 parts (by weight) of composition $A_1$
1 part of composition $B_4$
10 parts of oxidant 20 Volumes (comprising 6% of hydrogen peroxide)

In parallel, we prepared a formula of the prior art:

| | |
|---|---|
| Oleic alcohol polyglycerolated with 2 moles of glycerol | 4 |
| Oleic alcohol polyglycerolated with 4 moles of glycerol | 5.69 AS |
| Oleic acid | 3 |
| Oleic amine at 2 moles of ethylene oxide sold under the trade name ETHOMEEN O12 by the company Akzo | 7 |
| Diethylaminopropyl laurylaminosuccinamate, sodium salt at 55% A.S. | 3.0 AS |
| Oleic alcohol | 5 |
| Diethanolamide of oleic acid | 12 |
| Ethanol | 7 |
| Propylene glycol | 3.5 |
| Dipropylene glycol | 0.5 |
| Monomethyl ether of propylene glycol | 9 |
| Ammonium acetate | 0.8 |
| Potassium carbonate | 2 |
| Demineralized water q.s.f. | 100 g |

At the moment of use, the composition of the prior art was mixed weight for weight with oxidant 20 Volumes (comprising 6% of hydrogen peroxide).

The final concentration of potassium carbonate was the same in the mixture of the disclosure as in that of the prior art, namely 1 g %. The pH values of the two mixtures were 9.4±0.2.

Each mixture was then applied on a lock of natural chestnut hair (height of tone 5). The bath ratio "mixture/lock of hair" was respectively 10/1 (g/g). The holding time was 45 min at 27° C. At the end of this time, the locks of hair were rinsed, then washed with Elsève multivitamin shampoo.

The following table shows that the formula of the disclosure gave greater lightening than that of the prior art.

| | L* | a* | b* | ΔE*ab |
|---|---|---|---|---|
| Untreated hair | 20.1 | 3.3 | 3.6 | / |
| Hair treated with the mixture of the disclosure | 25.5 | 6.6 | 9.1 | 8.4 |
| Hair treated with the mixture of the prior art | 24.2 | 5.8 | 7.8 | 6.4 |

What is claimed is:

1. A method of coloring or lightening human keratin fibers in the presence of an oxidizing agent comprising application of the following to said fibers:
   an anhydrous cosmetic composition (A) comprising at least one fat and at least one surfactant;
   a composition (B) comprising at least one oxidizing agent; and
   a composition (C) comprising at least one inorganic base.

2. A method according to claim 1, wherein composition (C) further comprises at least one oxidation dye and/or at least one direct dye.

3. A method according to claim 1, wherein the at least one fat is chosen from $C_6$-$C_{16}$ lower alkanes, non-silicone oils of animal, vegetable, mineral or synthetic origin, fatty alcohols, fatty acids, fatty acid and/or fatty alcohol esters, non-silicone waxes, and silicones, or mixtures thereof.

4. A method according to claim 1, wherein at least one fat is chosen from $C_6$-$C_{16}$ lower alkanes, non-silicone oils of mineral or synthetic origin, fatty alcohols, fatty acid and/or fatty alcohol esters, and silicones, or mixtures thereof.

5. A method according to claim 1, wherein the at least one fat is chosen from liquid paraffin; polydecenes; and liquid esters of fatty acids or of fatty alcohols; or mixtures thereof.

6. A method according to claim 1, wherein the total fat content ranges from 10 to 99 wt. %, relative to the weight of composition (A).

7. A method according to claim 1, wherein the total fat content ranges from 20 and 90 wt. %, relative to the weight of composition (A).

8. A method according to claim 1, wherein the at least one surfactant present in composition (A) is a nonionic surfactant.

9. A method according to claim 8, wherein the at least one surfactant present in composition (A) is chosen from mono- or polyalkoxylated and mono- or polyglycerolated nonionic surfactants.

10. A method according to claim 1, wherein the total surfactant content ranges from 0.1 to 50 wt. %, relative to the weight of the anhydrous composition (A).

11. A method according to claim 1, wherein the total surfactant content ranges from 0.5 to 30 wt. %, relative to the weight of the anhydrous composition (A).

12. A method according to claim 1, wherein the at least one inorganic base has the following structure:

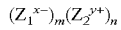

wherein
   $Z_2$ represents a metal from columns 1 to 13 of the periodic table of the elements;
   $Z_1^{x-}$ represents an anion chosen from the ions $CO_3^{2-}$, $OH^-$ $HCO_3^{2-}$, $SiO_3^{2-}$, $HPO_4^{2-}$, $PO_4^{3-}$, and $B_4O_7^{2-}$,
   x represents 1, 2, and 3;
   y represents 1, 2, 3, and 4; and
   m and n represent independently of one another 1, 2, 3, and 4
   with (n)(y)=(m)(x).

13. A method according to claim 12, wherein
   $Z_2$ represents a metal from columns 1 and 2 of the periodic table of the elements; and
   $Z_1^{x-}$ represents an anion chosen from the ions $CO_3^{2-}$, $OH^-$, and $SiO_3^{2-}$.

14. A method according to claim 1, wherein the at least one inorganic base is chosen from sodium carbonate, potassium carbonate, sodium hydroxide, potassium hydroxide, sodium metasilicate, and potassium metasilicate.

15. A method according to claim 1, wherein the at least one inorganic base is chosen from the alkali-metal carbonates.

16. A method according to claim 1, wherein the at least one inorganic base is present in an amount ranging from 0.01 to 30 wt. %, relative to the weight of composition (B).

17. A method according to claim 1, wherein the at least one inorganic base is present in an amount ranging from 0.1 to 20 wt. %, relative to the weight of composition (B).

18. A method according to claim 1, wherein compositions (A), (B) and (C) are applied successively and without intermediate rinsing.

19. A method according to claim 1, wherein a composition resulting from the mixing, prior to application, of compositions (A) and (C) and then the oxidizing composition (B) are applied successively and without intermediate rinsing.

20. A method according to claim 1, wherein a composition obtained by extemporaneous mixing, before application, of compositions (A), (B) and (C) is applied.

21. A method according to claim 1, wherein the weight ratios $R_1$ of the amounts of compositions (A)+(C)/(B) and $R_2$ of the amounts of compositions (A)/(C) range from 0.1 to 10.

22. A method according to claim 1, wherein the weight ratios $R_1$ of the amounts of compositions (A)+(C)/(B) and $R_2$ of the amounts of compositions (A)/(C) range from 0.3 to 3.

23. A kit comprising a first compartment comprising the anhydrous composition (A) comprising at least one fat and at least one surfactant, a second compartment comprising a composition (B) comprising at least one oxidizing agent, and a third compartment comprising a composition (C) comprising at least one inorganic base.

24. A kit according to claim 23, wherein composition (C) comprises at least one oxidation dye and/or at least one direct dye.

\* \* \* \* \*